US012573488B2

(12) United States Patent
Gaweda et al.

(10) Patent No.: US 12,573,488 B2
(45) Date of Patent: *Mar. 10, 2026

(54) SYSTEM AND METHOD FOR PERSONALIZED DOSING OF PHARMACOLOGIC AGENTS

(71) Applicant: University of Louisville Research Foundation, Inc., Louisville, KY (US)

(72) Inventors: Adam E. Gaweda, Jeffersonville, IN (US); Michael E. Brier, Rossville, TN (US); George R. Aronoff, Englewood, CO (US); Alfred A. Jacobs, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/663,322

(22) Filed: May 14, 2024

(65) Prior Publication Data

US 2024/0296928 A1 Sep. 5, 2024

Related U.S. Application Data

(63) Continuation of application No. 17/024,518, filed on Sep. 17, 2020, now abandoned, which is a
(Continued)

(51) Int. Cl.
| | |
|---|---|
| *G16H 20/10* | (2018.01) |
| *A61B 34/10* | (2016.01) |
| *G16H 50/20* | (2018.01) |
| *G16H 50/50* | (2018.01) |
| *G16Z 99/00* | (2019.01) |

(52) U.S. Cl.
CPC ............. *G16H 20/10* (2018.01); *A61B 34/10* (2016.02); *G16H 50/20* (2018.01); *G16H 50/50* (2018.01); *G16Z 99/00* (2019.02)

(58) Field of Classification Search
CPC ........ G16H 20/10; G16H 50/20; G16H 50/50; A61B 34/10; G16Z 99/00
See application file for complete search history.

(56) References Cited

U.S. PATENT DOCUMENTS

| | | | | |
|---|---|---|---|---|
| 8,449,471 | B2 * | 5/2013 | Tran ..................... | A61B 5/7225 600/485 |
| 2010/0292634 | A1 * | 11/2010 | Kircher, Jr. ............ | G06N 5/048 604/66 |

FOREIGN PATENT DOCUMENTS

| | | | | |
|---|---|---|---|---|
| CA | 2396573 A1 * | 7/2001 | ............. | G06F 17/00 |

* cited by examiner

*Primary Examiner* — Eliza A Lam
(74) *Attorney, Agent, or Firm* — Dentons Bingham Greenebaum LLP; Brian W. Chellgren

(57) ABSTRACT

A system and method for personalized dosing of a pharmacologic agent include: executing, using a processing device, a plurality of dosing regimen program modules to determine a respective plurality of dose sets in response to receiving, from an input device, a target response value for a patient; and executing, using the processing device, a dosing selection algorithm module, following executing the plurality of dosing regimen program modules and in response to receiving from the input device a response profile and a monitoring frequency of the patient, to determine a recommended dose set computed as a combination of the plurality of dose sets weighted by degrees of matching computed using fuzzy sets and the response profile.

20 Claims, 16 Drawing Sheets

Related U.S. Application Data continuation of application No. 15/812,666, filed on Nov. 14, 2017, now Pat. No. 10,803,142, which is a continuation of application No. 13/631,112, filed on Sep. 28, 2012, now Pat. No. 9,852,267.

(60) Provisional application No. 61/541,489, filed on Sep. 30, 2011.

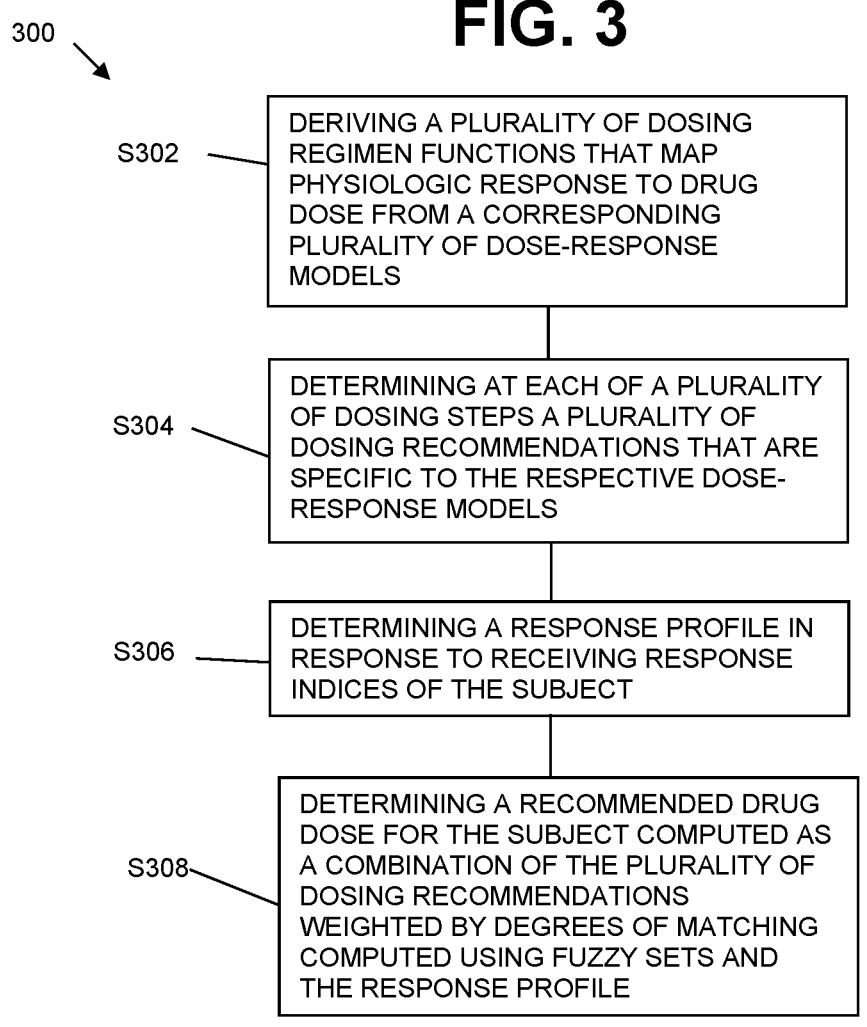

S302 — DERIVING A PLURALITY OF DOSING REGIMEN FUNCTIONS THAT MAP PHYSIOLOGIC RESPONSE TO DRUG DOSE FROM A CORRESPONDING PLURALITY OF DOSE-RESPONSE MODELS

S304 — DETERMINING AT EACH OF A PLURALITY OF DOSING STEPS A PLURALITY OF DOSING RECOMMENDATIONS THAT ARE SPECIFIC TO THE RESPECTIVE DOSE-RESPONSE MODELS

S306 — DETERMINING A RESPONSE PROFILE IN RESPONSE TO RECEIVING RESPONSE INDICES OF THE SUBJECT

S308 — DETERMINING A RECOMMENDED DRUG DOSE FOR THE SUBJECT COMPUTED AS A COMBINATION OF THE PLURALITY OF DOSING RECOMMENDATIONS WEIGHTED BY DEGREES OF MATCHING COMPUTED USING FUZZY SETS AND THE RESPONSE PROFILE

| $k$ | time step |
|---|---|
| $m,n$ | order parameters for Dose-Response Model $i$ |
| $R_k$ | physiologic response at time $k$ |
| $\Delta R_k$ | change in physiologic response at time $k$: $\Delta R_k = R_k - R_{k-1}$ |
| $R_{target}$ | target physiologic response |
| $D_k$ | drug dose at time $k$ |
| $D_{k,i}^*$ | optimal drug dose at time $k$ |

700

900

1100

SYSTEM AND METHOD FOR PERSONALIZED DOSING OF PHARMACOLOGIC AGENTS

CROSS-REFERENCE TO RELATED APPLICATIONS

This application is a continuation of prior application Ser. No. 17/024,518, filed Sep. 17, 2020, which is a continuation of prior application Ser. No. 15/812,666, filed Nov. 14, 2017, which is a continuation of prior application Ser. No. 13/631, 112, filed Sep. 28, 2012, which claims the benefit of U.S. Provisional Application No. 61/541,489, filed Sep. 30, 2011, the entire disclosures of which are incorporated herein by reference.

STATEMENT REGARDING FEDERALLY SPONSORED RESEARCH OR DEVELOPMENT

This invention was made with government support under Grant Nos. DK072085 and DK072085S01 awarded by the National Institutes of Health, and an individual Merit Award awarded by the Department of Veterans Affairs to Michael E. Brier. The government has certain rights in the invention.

TECHNICAL FIELD

The presently-disclosed subject matter relates to a system and method for personalized dosing of pharmacologic agents. In particular, the presently-disclosed subject matter relates to a computer-based system and method for personalized dosing of one or more pharmacologic agents to optimize one or more therapeutic responses.

BACKGROUND

Currently, a number of diseases and disorders are effectively treated and/or managed by administering various pharmacologic agents to the subjects that are suffering from those diseases and disorders. In this regard, and to provide standardized care for these subjects, a number of dosing regimens and guidelines have further been developed in recent years for each of the various pharmacologic agents. However, these dosing regimens and guidelines have often overlooked not only the complexity of the diseases and disorders being treated by the pharmacologic agents, but the dosing regimens and guidelines have also often overlooked the variability in the responses each particular subject may have to a particular pharmacologic agent, which may then lead to an adverse outcome.

For example, anemia in subjects suffering from end-stage renal disease (ESRD) is often effectively treated by the administration of erythropoiesis-stimulating agents (Epo), such as recombinant human erythropoietin, which increase the amount of red blood cells and hemoglobin found in these subjects. To facilitate the effective administration of Epo, the National Kidney Foundation-Kidney/Disease Outcomes Quality Initiative (NKF-K/DOQI) has developed and published guidelines on Epo dosing to achieve a target hemoglobin range (see National Kidney Foundation: NKF-K/DOQI Clinical Practice, Guidelines for Anemia of Chronic Kidney Disease: Update 2000. *Am. J. Kidney Dis.* 37: S182-S238, 2001). However, despite these guidelines, it is frequently observed that subjects move into, through, and out of the target hemoglobin range over the course of a year of treatment with Epo, and that only approximately one-third (38%) of the subjects are within the target range at any given time (see Lacson E, Ofsthun N, Lazarus J M: Effect of variability in anemia management on hemoglobin outcomes in ESRD. *Am. J. Kidney Dis.* 41: 111-124, 2003). This behavior is not surprising given the contribution of measurement error, the fact that subjects' responsiveness to Epo can change over time, and the economic and medical pressures to avoid falling below or to avoid exceeding specific levels of hemoglobin. Nevertheless, it has still been found that in subjects with chronic kidney disease, the poor management of hemoglobin levels can lead to an increased risk of adverse events.

Accordingly, a system and method for dosing pharmacologic agents, such as Epo, that allows more precise control over the dosing of the pharmacological agents, while also taking into account the variability among subjects and their responses, would be both highly desirable and beneficial.

BRIEF SUMMARY OF THE INVENTION

The presently-disclosed subject matter relates to systems and methods for personalized dosing of pharmacological agents. According to one embodiment of the invention, a system for personalized dosing of a pharmacologic agent includes: an input device; a data storage device; a plurality of dosing regimen program modules stored on the data storage device, each of the plurality of dosing regimen program modules for determining a dose set for a different specific pharmacologic agent sensitivity profile and monitoring frequency; a dosing selection algorithm module stored on the data storage device; and a processing device in communication with the input device and the data storage device. The processing device: executes the plurality of dosing regimen program modules to determine a respective plurality of dose sets in response to receiving from the input device a target response value for a patient; and further executes the dosing selection algorithm module, following executing the plurality of dosing regimen program modules and in response to receiving from the input device a response profile and a monitoring frequency of the patient, to determine a recommended dose set that is computed as a combination of the plurality of dose sets weighted by degrees of matching computed using fuzzy sets and the response profile.

According to an aspect of the invention, executing the plurality of dosing regimen program modules to determine a respective plurality of dose sets is further in response to receiving, from the input device, data on at least a current physiologic response value for the patient and data on at least a current dose value of the pharmacologic agent for the patient. When the patient has not received the drug before (i.e., when a treatment process is being initiated) the "current dose value" will be zero. Executing the plurality of dosing regimen program modules to determine a respective plurality of dose sets can further be in response to receiving from the input device data on past physiologic response values for the patient, and data on past dose values of the pharmacologic agent for the patient. Then, each of the plurality of dosing regimen program modules can include a dose-response model function and a dose optimizer routine. The dose optimizer routine can derive an optimal dose by iteratively sending a proposed new dose value to the dose-response model function, observing a predicted response produced by the dose-response model function, and optimizing an objective function value that mathematically formulates treatment objectives.

In some embodiments, the objective function value is determined substantially according to the function:

$OFV = w_{resp} f_{resp}$(Prediced Responses, Target Responses) +

$w_{dose,1} f_{dose,1}$(New Doses, Current Doses) +

$w_{dose,2} f_{dose,2}$(New Doses, Maximum Doses) + $w_{doseresp} f_{doseresp}$(New Doses, Current Doses, Predicted Responses, Current Responses)

where:

$f_{resp}$(Predicted Responses, Target Responses) compares the predicted response to the target response value;

$f_{dose,2}$(New Doses, Current Doses) compares the proposed new dose value to current dose value;

$f_{dose,2}$(New Doses, Maximum Doses) compares the proposed new dose value to a maximum doses value;

$f_{doseresp}$(New Doses, Current Doses, Predicted Responses, Current Responses) compares a change between the proposed new dose value and the current dose value with a change between the predicted response and the current physiologic response value; and $w_{resp}$, $w_{dose,1}$, $w_{dose,2}$, and $w_{doseresp}$ are weight coefficients that determines an influence of the respective terms on the OFV.

Further, in some embodiments, a number of the plurality of dosing regimen program modules is determined by multiplying a predetermined number of pharmacologic agent sensitivity profiles utilized by a predetermined number of monitoring frequencies utilized.

According to another aspect, the recommended dose set is determined substantially according to the function:

Recommended Dose Set = $w_{F1}(w_{R1}$ Dose Set$_1$ + ... + $w_{RN1}$ Dose Set$_{N1}$) +

... + $w_{FN2}(w_{R1}$ Dose Set$_{N-N1+1}$ + ... + $w_{RN1}$ Dose Set$_N$)

where:

$N_1$ is a number of pharmacologic agent sensitivity profiles of the plurality of dose sets;

$N_2$ is a number of monitoring frequencies of the plurality of dose sets;

N is a number of the plurality of dose sets equal to $N_1 \cdot N_{29}$;

$w_{F1}$, ..., $w_{FN2}$ are monitoring frequency weights defined as follows:

$w_{Fi}$=1 if a monitoring frequency matches that of the dose set;

$w_{Fi}$=0 otherwise;

$w_{R1}$, ..., $w_{RN1}$ are response index weights defined as follows:

$w_{Ri}$=1 if the response profile fully match a sensitivity profile of the dose set;

0<$w_{Ri}$<1 if the response profile partially match the sensitivity profile of the dose set;

and $w_{Ri}$=0 if the response profile does not match the sensitivity profile of the dose set; and the response index weights are computed using a fuzzy set approach.

In some embodiments, the dosing selection algorithm module further determines a time of next response measurement as a next time instance at which a current physiologic response value should be measured after the recommended dose set has been implemented.

According to another aspect of the invention, methods for personalized dosing of a pharmacologic agent are provided. In one implementation, a method for personalized dosing of a pharmacologic agent is provided that includes: executing, using a processing device, a plurality of dosing regimen program modules to determine a respective plurality of dose sets in response to receiving, from an input device, a target response value for a patient; and executing, using the processing device, a dosing selection algorithm module, following executing the plurality of dosing regimen program modules and in response to receiving from the input device a response profile and a monitoring frequency of the patient, to determine a recommended dose set computed as a combination of the plurality of dose sets weighted by degrees of matching computed using fuzzy sets and the response profile.

In one implementation, executing the plurality of dosing regimen program modules to determine a respective plurality of dose sets is further in response to receiving from the input device data on at least a current physiologic response value for the patient and data on at least a current dose value of the pharmacologic agent for the patient. When the patient has not received the drug before (i.e., when a treatment process is being initiated) the "current dose value" will be zero. Executing the plurality of dosing regimen program modules to determine a respective plurality of dose sets can further be in response to receiving from the input device data on past physiologic response values for the patient, and data on past dose values of the pharmacologic agent for the patient. This implementation can further include a dose optimizer routine of each of the plurality of dosing regimen program modules executing on the processing device. Then, the dose optimizer routine can: derive an optimal dose by iteratively sending a proposed new dose value to a dose-response model function; observe a predicted response produced by the dose-response model function; and optimize an objective function value that mathematically formulates treatment objectives.

In accord with this implementation, the method can further include determining the objective function value substantially according to the function:

$OFV = w_{resp} f_{resp}$(Prediced Responses, Target Responses) +

$w_{dose,1} f_{dose,1}$(New Doses, Current Doses) +

$w_{dose,2} f_{dose,2}$(New Doses, Maximum Doses) + $w_{doseresp} f_{doseresp}$(New Doses, Current Doses, Predicted Responses, Current Responses)

where:

$f_{resp}$(Predicted Responses, Target Responses) compares the predicted response to the target response value;

$f_{dose,1}$(New Doses, Current Doses) compares the proposed new dose value to current dose value;

$f_{dose,2}$(New Doses, Maximum Doses) compares the proposed new dose value to a maximum doses value;

$f_{doseresp}$(New Doses, Current Doses, Predicted Responses, Current Responses) compares a change between the proposed new dose value and the current dose value with a change between the predicted response and the current physiologic response value; and $w_{resp}$, $w_{dose,1}$, $w_{dose,2}$, and $w_{doseresp}$ are weight coefficients that determines an influence of the respective terms on the OFV.

Further, in some implementations, the method includes determining a number of the plurality of dosing regimen program modules by multiplying a predetermined number of pharmacologic agent sensitivity profiles utilized by a pre-determined number of monitoring frequencies utilized.

In another implementation, the method additionally includes determining, by the dosing selection algorithm module, the recommended dose set substantially according to the function:

$$\text{Recommended Dose Set} = w_{F1}(w_{R1} \text{ Dose Set}_1 + \dots + w_{RN1} \text{ Dose Set}_{N1}) +$$
$$\dots + w_{FN2}(w_{R1} \text{ Dose Set}_{N-N1+1} + \dots + w_{RN1} \text{ Dose Set}_N)$$

where:

$N_1$ is a number of pharmacologic agent sensitivity profiles of the plurality of dose sets;

$N_2$ is a number of monitoring frequencies of the plurality of dose sets;

N is a number of the plurality of dose sets equal to $N_1 \cdot N_2$;

$w_{F1}, \dots, w_{FN2}$ are monitoring frequency weights defined as follows:

$w_{Fi}=1$ if a monitoring frequency matches that of the dose set;

$w_{Fi}=0$ otherwise;

$w_{R1}, \dots, w_{RN1}$ are response index weights defined as follows:

$w_{Ri}=1$ if the response profile fully match a sensitivity profile of the dose set;

$0<w_{Ri}<1$ if the response profile partially match the sensitivity profile of the dose set; and $w_{Ri}=0$ if the response profile does not match the sensitivity profile of the dose set; and the response index weights are computed using a fuzzy set approach.

In certain implementations, the method further includes determining, by the dosing selection algorithm module, a time of next response measurement as a next time instance at which a current physiologic response value should be measured after the recommended dose set has been implemented.

In accordance with yet another aspect of the invention, a system for personalized dosing of an erythropoietic stimulating agent (Epo) for managing anemia in a subject includes: a data storage device for storing data and program instructions; a processing device; an input device for receiving a target hemoglobin value ($Hb_{target}$), a current hemoglobin value ($Hb_k$), a rate of change of hemoglobin value ($\Delta Hb_k$), and a previous Epo dose prescribed value ($Epo_k$) related to an amount of Epo being received by the subject; "i" dosing regimen program modules stored in the data storage device and including instructions for causing the processing device to determine an initial recommended Epo dose ($Epo_{k+1,i}*$) for each of i dosing regimens; and a dosing selection algorithm module stored in said data storage device and including instructions for causing the processing device to determine a next recommended Epo dose ($Epo_{k+1}$).

In one embodiment, the Hbx value is computed from Hb data collected over a predetermined time period using low-ess smoothing. In some embodiments, the predetermined time period can comprise a 28 day window. In some embodiments, a $\Delta Hb_k$ value can be computed from Hb data collected over a predetermined time period (e.g., a 28 day window) using lowess smoothing. In some embodiments, the $Epo_k$ value can be the dose prescribed in a preceding dose step or can be computed from Epo data over a predetermined time period, where, again, the predetermined time period can comprise a 28 day window.

In another embodiment, each of the "i" dosing regimen program modules includes: a dose-response model module for causing the processing device to use a dose-response model to determine a $Hb_{k+1}$ value and a predicted Hb response value ($\Delta Hb_{k+1}$) for a subject with a respective Epo sensitivity profile based on the $Hb_k$ value, the $\Delta Hb_k$ value, and a proposed $Epo_{k+1}$ value; and an optimization algorithm module for causing the processing device to use an optimization algorithm to determine the $Epo_{k+1,i}*$ value by determining a proposed $Epo_{k+1}$ value using the $Hb_{target}$ value, the $Epo_k$ value, the $Hb_{k+1}$ value and the $\Delta Hb_{k+1}$ value, and then iteratively providing the proposed $Epo_{k+1}$ value to the dose-response model module and re-determining the proposed $Epo_{k+1}$ value until the proposed $Epo_{k+1}$ values converge to the $Epo_{k+1,i}*$ value.

In some embodiments, the dose-response model is substantially according to the function:

$$\begin{bmatrix} \dfrac{dHb}{dt} \\ \dfrac{d\Delta Hb}{dt} \end{bmatrix} = \begin{bmatrix} \dfrac{-2}{T_i} & \dfrac{1}{T_i^2} \\ 1 & 0 \end{bmatrix} \begin{bmatrix} Hb \\ \Delta Hb \end{bmatrix} + \begin{bmatrix} \dfrac{K_i}{T_i^2} \\ 0 \end{bmatrix} Epo$$

where:

$K_i$—erythropoietic response (1,000 Units Epo per 1 g/dL Hb change)

$T_i$—time constant

Epo—dose (1,000 Units)

Hb—hemoglobin level (g/dL)

$\Delta Hb$—hemoglobin rate of change (g/dL per day); and wherein the optimization algorithm is substantially according to the function:

$$OVF = \sum_{k_p=1}^{H_p} \left(Hb_{target} - Hb_{k_p}\right)^2 + \lambda_i \sum_{k_c=1}^{H_c} \Delta Epo_{k_c}^2$$

where:

$k_p$, $k_c$—time steps (weeks)

$H_p$—prediction horizon (weeks)

$H_c$—control horizon (weeks)

$\lambda_i$—dose change suppression (non-dimensional)

$Hb_{kp}$—hemoglobin at step $k_p$ $\Delta Epo_{kc}$—change in dose from step $k_{c-1}$ to $k_c$;

subject to constraints:

$$0 \le Epo \le 90{,}000 \text{ units per week}$$
$$0 \le Hb \le 20 \text{ g/dL}$$
$$-0.5 < \Delta Hb < 0.5 \text{ g/dL per week}$$

where: $\Delta Hb = Hb_{kp} - Hb_{kp-1}$.

According to another feature, "i" can equal 5 such that there are 5 dosing regimens; and the dosing selection algorithm module may determine the $Epo_{k+1}$ value substantially according to the equation:

$$Epo_{k+1} = \frac{w_{R1}Epo_{k+1,1}^* + w_{R2}Epo_{k+1,2}^* + w_{R3}Epo_{k+1,3}^* + w_{R4}Epo_{k+1,4}^* + w_{R5}Epo_{k+1,5}^*}{w_{R1} + w_{R2} + w_{R3} + w_{R4} + w_{R5}}$$

where:

| | | | |
|---|---|---|---|
| $w_{R1} = f_{MF}(\text{Epo}_k, \mu_1, s_{1l}, s_{1r})$ | $\mu_1 = 0$ | $s_{1l} = 1.0$ | $s_{1r} = 0.9*(\text{Hb}_{target} - \text{Hb}_0)$ |
| $w_{R2} = f_{MF}(\text{Epo}_k, \mu_2, s_{2l}, s_{2r})$ | $\mu_2 = 3*(\text{Hb}_{target} - \text{Hb}_0)$ | $s_{2l} = s_{1r}$ | $s_{2r} = 1.35*(\text{Hb}_{target} - \text{Hb}_0)$ |
| $w_{R3} = f_{MF}(\text{Epo}_k, \mu_3, s_{3l}, s_{3r})$ | $\mu_3 = 7.5*(\text{Hb}_{target} - \text{Hb}_0)$ | $s_{3l} = s_{2r}$ | $s_{3r} = 2.25*(\text{Hb}_{target} - \text{Hb}_0)$ |
| $w_{R4} = f_{MF}(\text{Epo}_k, \mu_4, s_{4l}, s_{4r})$ | $\mu_4 = 15*(\text{Hb}_{target} - \text{Hb}_0)$ | $s_{4l} = s_{3r}$ | $s_{4r} = s_{4l}$ |
| $w_{R5} = f_{MF}(\text{Epo}_k, \mu_5, s_{5l}, s_{5r})$ | $\mu_5 = 22.5*(\text{Hb}_{target} - \text{Hb}_0)$ | $s_{5l} = s_{4r}$ | $s_{5r} = 100.0$ | and where $f_{MF}$ is a fuzzy membership function substantially according to the equation:

$$f_{MF}(x, \mu, s_l, s_r) = \begin{cases} \exp\left(-\dfrac{(x-\mu)^2}{s_l^2}\right) & x < \mu \\ 1 & x = \mu \\ \exp\left(-\dfrac{(x-\mu)^2}{s_r^2}\right) & x > \mu \end{cases}$$

In accordance with still yet another aspect of the invention, a method for personalized dosing of erythropoietic stimulating agents (Epo) for managing anemia is provided. In one exemplary implementation, a method for personalized dosing of Epo is provided and includes: receiving, via an input device, a target hemoglobin value ($\text{Hb}_{target}$), a current hemoglobin value ($\text{Hb}_k$), a rate of change of hemoglobin value ($\Delta\text{Hb}_k$), and an Epo dose received value ($\text{Epo}_k$) related to an amount of Epo being received by the subject; determining, by a processing device executing instructions of "i" dosing regimen program modules stored in a data storage device, an initial recommended Epo dose ($\text{Epo}_{k+1,i}$*) for each of i dosing regimens; and determining, by the processing device executing instructions of a dosing selection algorithm module stored in said data storage device, a next recommended Epo dose ($\text{Epo}_{k+1}$).

In one implementation, the Hbx value is computed from Hb data collected over a predetermined time period using lowess smoothing. In some implementations, the predetermined time period can comprise a 28 day window. In some implementations, a $\Delta\text{Hb}_k$ value can be computed from Hb data collected over a predetermined time period (e.g., a 28 day window) using lowess smoothing. In some implementations, the $\text{Epo}_k$ value can be computed from Epo data over a predetermined time period (e.g., a 28 day window) or can be computed as an average weekly Epo dose received.

In accordance with another implementation, a method for personalized dosing of Epo further includes: determining, by the processing device executing instructions of a dose-response model module using a dose-response model, a $\text{Hb}_{k+1}$ value and a predicted hemoglobin response value ($\Delta\text{Hb}_{k+1}$) for a subject with a respective Epo sensitivity profile based on the Hbx value, the $\Delta\text{Hb}_k$ value, and a proposed $\text{Epo}_{k+1}$ value; and determining, by the processing device executing instructions of an optimization algorithm module using an optimization algorithm, the $\text{Epo}_{k+1,i}$* value by determining the proposed $\text{Epo}_{k+1}$ value using the $\text{Hb}_{target}$ value, the $\text{Epo}_k$ value, the $\text{Hb}_{k+1}$ value and the $\Delta\text{Hb}_{k+1}$ value, and then iteratively providing a proposed $\text{Epo}_{k+1}$ value to the dose-response model module and re-determining the proposed $\text{Epo}_{k+1}$ value until the proposed $\text{Epo}_{k+1}$ values converge to the $\text{Epo}_{k+1,i}$* value.

In some implementations, the dose-response model is substantially according to the function:

$$\begin{bmatrix} \dfrac{dHb}{dt} \\ \dfrac{d\Delta Hb}{dt} \end{bmatrix} = \begin{bmatrix} \dfrac{-2}{T_i} & \dfrac{1}{T_i^2} \\ 1 & 0 \end{bmatrix} \begin{bmatrix} Hb \\ \Delta Hb \end{bmatrix} + \begin{bmatrix} \dfrac{K_i}{T_i^2} \\ 0 \end{bmatrix} Epo \tag{4}$$

where:

$K_i$—erythropoietic response (1,000 Units Epo per 1 g/dL Hb change)

$T_i$—time constant

Epo—dose (1,000 Units)

Hb—hemoglobin level (g/dL)

$\Delta$Hb—hemoglobin rate of change (g/dL per day); and wherein the optimization algorithm is substantially according to the function:

$$OFV = \sum_{k_p=1}^{H_p} \left(Hb_{target} - Hb_{k_p}\right)^2 + \lambda_i \sum_{k_c=1}^{H_c} \Delta Epo_{k_c}^2 \tag{6}$$

where:

$k_p$, $k_c$—time steps (weeks)

$H_p$—prediction horizon (weeks)

$H_c$—control horizon (weeks)

$\lambda_i$—dose change suppression (non-dimensional)

$Hb_{kp}$—hemoglobin at step $k_p$ $\Delta Epo_{kc}$—change in dose from step $k_{c-1}$ to $k_c$;

subject to constraints:

$$0 \leq Epo \leq 90{,}000 \text{ units per week}$$

$$0 \leq Hb \leq 20 \text{ g/dL}$$

$$-0.5 < \Delta Hb < 0.5 \text{ g/dL per week}$$

where: $\Delta Hb = Hb_{kp} - Hb_{kp-1}$.

According to yet another implementation, "i" may equal 5 such that there are 5 dosing regimens; and the dosing selection algorithm module can determine an $\text{Epo}_{next}$ value substantially according to the equation:

$$Epo_{k+1} =$$

$$\frac{w_{R1}Epo^*_{k+1,1} + w_{R2}Epo^*_{k+1,2} + w_{R3}Epo^*_{k+1,3} + w_{R4}Epo^*_{k+1,4} + w_{R5}Epo^*_{k+1,5}}{w_{R1} + w_{R2} + w_{R3} + w_{R4} + w_{R5}}$$

where:

| | | | |
|---|---|---|---|
| $w_{R1} = f_{MF}(\text{Epo}_k, \mu_1, s_{1l}, s_{1r})$ | $\mu_1 = 0$ | $s_{1l} = 1.0$ | $s_{1r} = 0.9*(\text{Hb}_{target} - \text{Hb}_0)$ |
| $w_{R2} = f_{MF}(\text{Epo}_k, \mu_2, s_{2l}, s_{2r})$ | $\mu_2 = 3*(\text{Hb}_{target} - \text{Hb}_0)$ | $s_{2l} = s_{1r}$ | $s_{2r} = 1.35*(\text{Hb}_{target} - \text{Hb}_0)$ |

-continued

| | | | |
|---|---|---|---|
| $w_{R3} = f_{MF}(Epo_k, \mu_3, s_{3l}, s_{3r})$ | $\mu_3 = 7.5*(Hb_{target} - Hb_0)$ | $s_{3l} = s_{2r}$ | $s_{3r} = 2.25*(Hb_{target} - Hb_0)$ |
| $w_{R4} = f_{MF}(Epo_k, \mu_4, s_{4l}, s_{4r})$ | $\mu_4 = 15*(Hb_{target} - Hb_0)$ | $s_{4l} = s_{3r}$ | $s_{4r} = s_{4l}$ |
| $w_{R5} = f_{MF}(Epo_k, \mu_5, s_{5l}, s_{5r})$ | $\mu_5 = 22.5*(Hb_{target} - Hb_0)$ | $s_{5l} = s_{4r}$ | $s_{5r} = 100.0$ | and where $f_{MF}$ is a fuzzy membership function substantially according to the equation:

$$f_{MF}(x, \mu, s_t, s_r) = \begin{cases} \exp\left(-\dfrac{(x-\mu)^2}{s_i^2}\right) & x < \mu \\ 1 & x = \mu \\ \exp\left(-\dfrac{(x-\mu)^2}{s_r^2}\right) & x > \mu \end{cases}.$$

Other features and advantages of the invention will be set forth in or apparent from the detailed description of exemplary embodiments of the invention found below.

BRIEF DESCRIPTION OF THE DRAWINGS

Illustrative aspects of the invention will be described in detail with reference to the following figures wherein:

FIG. 3 is a flow chart of an exemplary method for personalized dosing of pharmacologic agents according to the invention.

FIG. 5 is a block diagram of another embodiment of a system for personalized dosing of pharmacologic agents according to the invention.

DESCRIPTION OF EXEMPLARY EMBODIMENTS OF THE INVENTION

Figure 1:
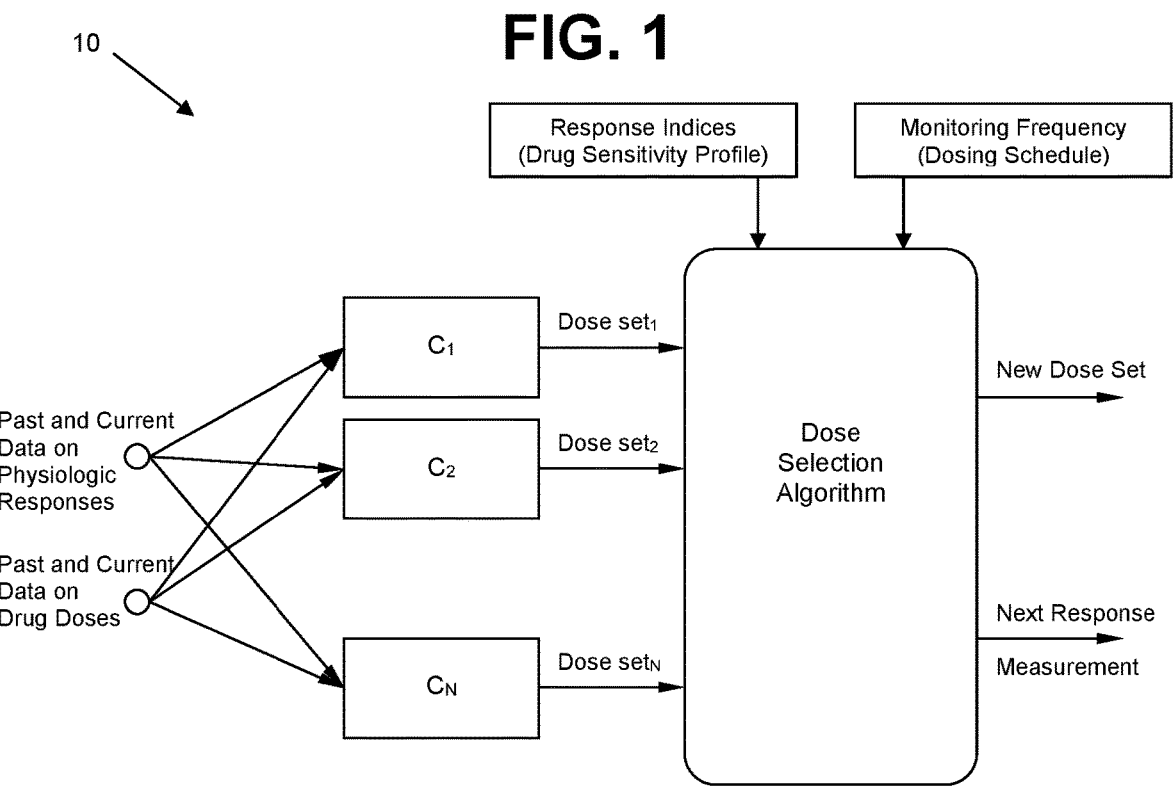
FIG. 1 is a block diagram of an embodiment of a system for personalized dosing of pharmacologic agents according to the invention.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the following terms are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The term "processing device" is used herein to describe one or more microprocessors, microcontrollers, central processing units, Digital Signal Processors (DSPs), Field-Programmable Gate Arrays (FPGAs), Application-Specific Integrated Circuits (ASICs), or the like for executing instructions stored on a data storage device.

The term "data storage device" is understood to mean physical devices (computer readable media) used to store programs (sequences of instructions) or data (e.g. program state information) on a non-transient basis for use in a computer or other digital electronic device, including primary memory used for the information in physical systems which are fast (i.e. RAM), and secondary memory, which are physical devices for program and data storage which are slow to access but offer higher memory capacity. Traditional secondary memory includes tape, magnetic disks and optical discs (CD-ROM and DVD-ROM). The term "memory" is often (but not always) associated with addressable semiconductor memory, i.e. integrated circuits consisting of silicon-based transistors, used for example as primary memory but also other purposes in computers and other digital electronic devices. Semiconductor memory includes both volatile and non-volatile memory. Examples of non-volatile memory include flash memory (sometimes used as secondary, sometimes primary computer memory) and ROM/PROM/EPROM/EEPROM memory. Examples of volatile memory include dynamic RAM memory, DRAM, and static RAM memory, SRAM.

The term "pharmacologic agent" is used herein to refer to any agent capable of effecting a measurable change in a physiological characteristic of a subject. Exemplary pharmacological agents discussed herein include, but are not limited to: erythropoietic stimulating agents, which are capable of affecting a change in the amounts of red blood cells and hemoglobin in a subject; injectable and oral iron supplements, which are capable of affecting a change in serum iron levels, serum ferritin levels, and transferrin saturation in a subject; injectable and oral hypoglycemic agents, such as insulin, which are capable of affecting a change in the levels of blood glucose found in a subject; hypertensive agents, such as alpha blockers, beta blockers, angiotensin converting enzyme inhibitors, angiotensin receptor blockers, direct vasodilators, direct renin inhibitors, calcium channel blockers, and diuretics, which are capable of affecting a change in blood pressure in a subject; immunosuppressive agents, such as calcineurin inhibitors, mycophenylate, and corticosteroids, which are capable of affecting plasma pharmacologic agent levels, rejection rates, and functional measures of immunity, agents for the treatment of gout, such as xanthine oxidase inhibitors, which are capable of affecting serum uric acid levels; and anticoagulation agents, such as warfarin, heparin, and enoxaparin, which are capable of affecting a change in the international normalized ratio (INR) observed in a subject (warfarin); partial thromboplastin time or clotting time observed in a subject (heparin), and anti-factor 10A observed in a subject (enoxaparin). In some embodiments, the term "pharmacologic agent" is used interchangeably with the term "drug."

The presently-disclosed subject matter relates to a system and method for personalized dosing of pharmacological agents and, in particular, a computer-based multiple model predictive control system and method for the personalized dosing of one or more pharmacologic agents that can be used to optimize one or more therapeutic responses in a subject. In some embodiments of the presently-disclosed subject matter, the underlying methodology of a computer-based system for personalized dosing of one or more pharmacologic agents is based on the principles of Multiple Model Predictive Control (MMPC).

The MMPC system used in accordance with the presently-disclosed subject matter contains multiple controllers, where an individual controller is an appropriately designed mathematical function describing a dosing regimen for: 1) an individual subject with specific degrees of sensitivity to the administered pharmacologic agents (i.e., pharmacologic agent or pharmacologic agent sensitivity profile); and 2) a specific dosing schedule (monitoring frequency). The dosing regimen is designed to achieve a user specified physiologic response and/or other treatment objectives to a high degree of accuracy in the presence of anticipated and/or unanticipated disturbances that can affect the subject's response to the pharmacologic agents, such as measurement noise, changes in the subject's physiologic response that are caused by factors other than the pharmacologic agents of interest, and changes in subject's pharmacologic agent sensitivity due to various clinical events such as hospitalization.

Referring first to FIG. 1, FIG. 1 shows a block diagram of an embodiment of an exemplary system 10 for personalized dosing of pharmacologic agent(s) in accordance with the presently-disclosed subject matter. In FIG. 1, $C_1, C_2, \ldots, C_N$ are individual controllers, where each controller receives data on past and current physiologic responses of interest, for example a level and a rate of change, as well as past and current pharmacologic agent doses. Based on this information, the exemplary system 10 computes new dose sets for each administered pharmacologic agent (Dose $set_1$, Dose $set_2$, . . . , Dose $set_N$) for various pharmacologic agent sensitivity profiles and monitoring frequencies. After all the dose sets are computed, they are fed to a Dose Selection Algorithm.

In addition to the dose recommendations (Dose $set_1$, Dose $set_2$, . . . , Dose $set_N$) produced by the controllers ($C_1$, $C_2, \ldots, C_N$), the Dose Selection Algorithm receives data on Response Indices (a response profile) of the treated subject and a Monitoring Frequency. Response Indices include, but are not limited to, any measured or computed physiologic, pharmacologic, genomic, or proteomic quantities indicative of a specific pharmacologic agent sensitivity profile, while the Monitoring Frequency is the rate at which the physiologic responses are measured and pharmacologic agent doses adjusted. The Response Indices provide quantitative information about the similarity between an individual subject's sensitivity profile to the pharmacologic agent at the time when the Response Index value was measured and the pharmacologic agent sensitivity profiles for which the controllers ($C_1$,$C_2$, . . . ,$C_N$) are designed. In some embodiments, various levels of single or multiple Response Indices can be associated with a specific sensitivity profile. In some embodiments, a Response Index is, for an example, the dose of the pharmacologic agent that is being prescribed to a subject to achieve a specific physiologic response. In this regard, in some embodiments, if a subject requires a small dose to achieve a certain response threshold, such a finding can indicate a high sensitivity to the prescribed pharmacologic agent. In other embodiments, if a subject requires a large dose to achieve the same response, such a finding can indicate a low sensitivity to the prescribed pharmacologic agent.

Upon receiving the dose recommendations produced by the controllers, and the data on the Response Indices and the Monitoring Frequency, the Dose Selection Algorithm subsequently produces a New Dose Set, where the New Dose Set is calculated as a weighted average of the individual dose recommendations, as follows:

$$\text{New Dose Set} = w_{F1}(w_{R1}\text{Dose Set}_1 + \ldots + w_{RN1}\text{Dose Set}_{N1}) + \quad (A)$$
$$\ldots + w_{FN2}(w_{R1}\text{Dose Set}_{N-N1+1} + \ldots + w_{RN1}\text{Dose Set}_N)$$

where $w_{F1}$, . . . , $w_{FN2}$ are the "monitoring frequency weights" defined as follows:
$w_{Fi}=1$ if the Monitoring Frequency matches that of controller $C_i$;
$w_{Fi}=0$ otherwise;
and $N_2$ is the number of possible monitoring frequencies;
and $w_{R1}$, . . . , $w_{RN1}$ are the "response index weight" defined as follows:
$w_{Ri}=1$ if the Response Indices fully match the sensitivity profile of controller $C_i$;
$0<w_{Ri}<1$ if the Response Indices partially match the sensitivity profile of controller $C_i$; and
$w_{Ri}=0$ if the Response Indices do not match sensitivity profile of controller $C_i$;
and $N_1$ is the number of pharmacologic agent sensitivity profiles;
and $N=N_1N_2$.

To allow partial matching between the Response Indices and the pharmacologic agent sensitivity profiles, the Response Index weights are calculated using a fuzzy set (fuzzy membership function) approach. Two exemplary methods to determine the location and shape of the fuzzy sets (fuzzy membership functions) are: 1) using prior knowledge of the dose-response characteristics, the designer may decide on the number, the location(s) and the half-width(s) of the fuzzy membership functions; and 2) the designer initially decides on the number, locations, and the shapes of the fuzzy sets (point 1) and then uses computer simulation to fine tune the number, the locations, and the shapes of the fuzzy sets.

With respect to the first exemplary method, each fuzzy set (membership function) corresponds to an individualized dosing regimen. The location of the fuzzy set, i.e. the coordinate of the maximum set value (1.0) determines the typical patient for whom that dosing regimen is optimal. The shape (width) of the fuzzy set determines the range of patients for whom that dosing regimen is approximately optimal. The half-widths of the fuzzy sets are typically selected such that neighboring fuzzy sets intersect at the same value (called alpha-cut). For example, in in the specific embodiment described below, the alpha-cut value is 0.25.

With respect to the second exemplary method, in the computer simulation, the dosing system is tested against a range of patient models with different dose-response profiles, or response characteristics (index), for example represented by patients' sensitivity to the pharmacologic agent, for a feasible range representing patient characteristics occurring in the real world. These models can, but do not have to, have the same structure as the models used to design the dosing regimens. During the simulation, the objective of the dosing system is to generate and send to the patient model doses which minimize the difference between the model simulated outcome and the end user-specified target(s) over end user-specified time period(s). This objective can be numerically expressed by a number of performance measures that quantify the difference between the target and the achieved outcome. Examples of such performance measures include Mean Absolute Difference (between outcome and target) or Mean Square Difference. The end user can specify that the system should not exceed certain threshold values for these performance measures for any of the simulated patients. If the dosing system exceeds one or more of those threshold values for one or more patient(s), it is said that the system does not meet the performance requirements for that (those) patient(s).

If during the simulation, the designer finds that the system does not meet performance requirements for a specific simulated patient, it means that the system does not contain an (approximately) optimal dosing regimen for that individual. In that case, an optimal dosing regimen is created for the subject (as described elsewhere in the application). To select that dosing regimen, a new fuzzy set is created and placed at the location representing response characteristic (index) of the said patient. The half-widths of this new set, as well as of the two neighboring sets are adjusted such that all neighboring sets intersect at the same value.

After performing this step, the simulation is repeated from the beginning. If another simulated patient is found where the performance requirements are not met, the above-described process of adding new dosing regimen and a new fuzzy set is repeated.

Furthermore, a time of Next Response Measurement is also produced by the Dose Selection Algorithm and is the next time instance at which the physiologic responses should be measured after the dose adjustment. This quantity is a function of the dose adjustment magnitude and the current physiologic response levels with relation to their targets, and depends on the specific pharmacologic agent dosing problem.

Figure 2:
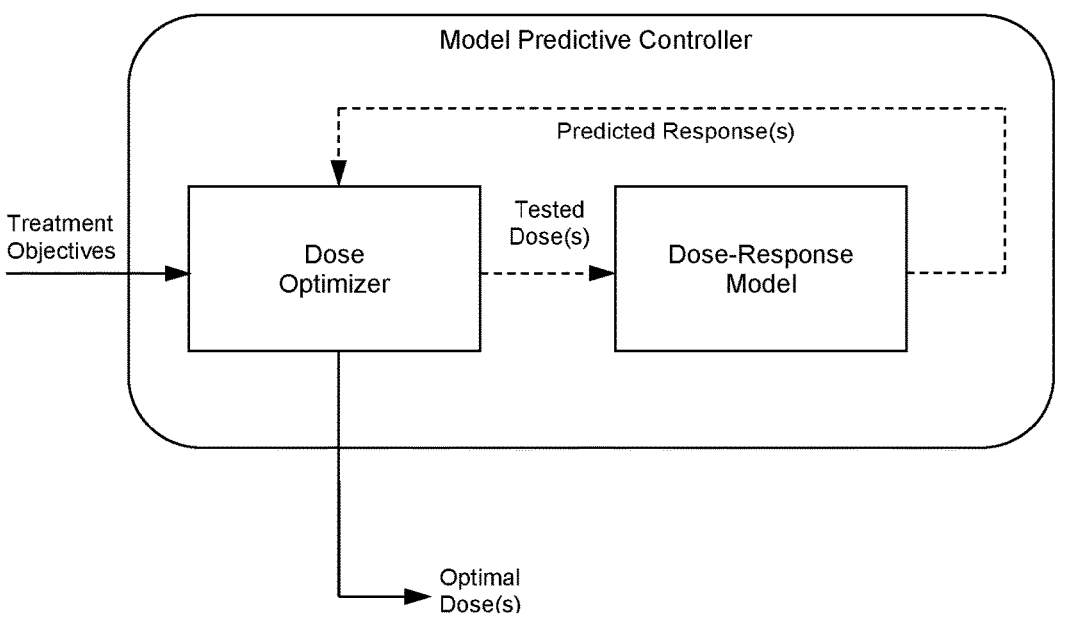
FIG. 2 is a block diagram of an exemplary Model Predictive Control methodology according to the invention.

Turning now to FIG. 2, FIG. 2 shows a block diagram of an exemplary Model Predictive Control (MPC) methodology that is used to derive controllers $C_1$,$C_2$, . . . ,$C_N$. The key components of the MPC as applied to pharmacologic agent dosing are: 1) Dose-Response Model; and 2) Dose Optimizer. Based on the user specified Treatment Objectives, the Dose Optimizer derives an Optimal Dose(s) by iteratively sending Tested Dose(s) to the Dose-Response Model, observing the Predicted Response(s) produced by the Dose-Response Model, and maximizing or minimizing the Objective Function Value (OFV) that mathematically formulates the Treatment Objectives:

$$OFV = w_{resp}f_{resp}(\text{Predicted Responses, Target Responses}) + \quad (B)$$

$$w_{dose,1}f_{dose,1}(\text{New Doses, Current Doses}) +$$

$$w_{dose,2}f_{dose,2}(\text{New Doses, Maximum Doses}) + w_{doseresp}f_{doseresp}$$

$$(\text{New Doses, Current Doses, Predicted Responses, Current Responses})$$

The first term, $f_{resp}$(Predicted Responses, Target Responses), compares the Predicted Responses to the Target Responses, specified by the user in the Treatment Objectives. A goal of this term is to ascertain that the derived dosing regimen maintains the physiologic responses of interest close to the levels specified by the user in the Treatment Objectives. The Target Responses can be represented by numbers or intervals. The function $f_{resp}$ approaches its maximum (minimum) value when the Predicted Responses meet the Target Responses and it decreases (increases) as the Predicted Responses move away from the Target Responses. The weight coefficient $w_{resp}$ determines the influence of this term on the overall OFV.

The second term, $f_{dose,1}$(New Doses, Current Doses), compares New Doses to Current Doses. A goal of this term is to minimize the magnitude of dose adjustments in order to prevent unnecessary dose changes due to random disturbances in the physiologic responses of interest. The function $f_{dose,1}$ achieves its maximum (minimum) value when the New Doses are the same as the Current Doses and it decreases (increases) as the New Doses move away from the Current Doses. The weight coefficient $w_{dose,1}$ determines the influence of this term on the overall OFV.

The third term, $f_{dose,2}$(New Doses, Maximum Doses), compares the New Doses to the Maximum Doses specified by the user in the Treatment Objectives. The Maximum Doses are typically set to protect the subject from pharmacologic agent toxicity or other dangerous side effects. A goal of this term is to thus prevent the case in which the New Doses for one or more of the administered pharmacologic agents exceed their corresponding Maximum Doses. The function $f_{dose,2}$ achieves its maximum (minimum) value when New Doses are zero and it decreases (increases) as the New Doses approach the Maximum Doses. The weight coefficient $w_{dose,2}$ determines the influence of this term on the overall OFV.

The fourth term, $f_{doseresp}$(New Doses, Current Doses, Predicted Responses, Current Reponses), compares the change in doses of the administered pharmacologic agents to the change in physiologic responses of interest. The goal of this term is to maximize the cost-effectiveness of the treatment. The function $f_{doseresp}$ achieves its maximum (minimum) value when the ratio of change in response to dose change is the largest. The weight coefficient $w_{doseresp}$ determines the influence of this term on the overall OFV.

Whether or not a term is included in the OFV formula and the specific form of each function ($f_{resp}$, $f_{dose,1}$, $f_{dose,2}$, $f_{doseresp}$) typically depends on the type of the dosing problem, the treatment objectives, and other user requirements. The terms ($f_{resp}$, $f_{dose,1}$, $f_{dose,2}$, $f_{doseresp}$) are computed using the Tested Doses and the Predicted Responses generated by the Dose-Response Model from the current time instance up to several time steps into the future. The number of future time steps over which the Predicted Responses are generated is called a Prediction Horizon and is a design parameter. The number of future time steps over which the Tested Doses fed to the Dose-Response Model is called a Control Horizon and is another design parameter. At all times, the Control Horizon must generally be less than or equal to the Prediction Horizon. The other design parameters are the weight coefficients ($w_{resp}$, $w_{dose,1}$, $w_{dose,2}$, $w_{doseresp}$). For a fixed Dose-Response Model, all the design parameters are chosen through iterative simulation in order to achieve specific performance measures. These performance measures include, but are not limited to: 1) time to achieve the Target Response from an initial state; and 2) stability of Physiologic Response in presence of measured and/or unmeasured disturbances once Target Response is achieved. These and possibly other performance measures are specified by the user before the controller design.

With further respect to the MPC methodology, the individual, subject-specific pharmacologic agent sensitivity profile is generally represented in the MPC methodology by a fixed Dose-Response Model. Individual controllers within the MMPC system have their own fixed Dose-Response Models that represent a specific pharmacologic agent sensitivity profile. In this regard, the controller design process is performed for each pharmacologic agent sensitivity profile and each monitoring frequency individually, while the number of individual controllers across the full spectrum of pharmacologic agent sensitivity profiles, denoted by $N_1$, is determined a priori by the designer. The number of individual controllers across the full spectrum of monitoring frequencies, denoted by $N_2$, generally depends on the number of monitoring frequencies used in a specific treatment of interest, with the total number of individual controllers being: $N=N_1N_2$.

Regardless of the number of controllers, however, each individual controller takes as input vector data on past and current responses of interest, past and current doses of administered pharmacologic agents, and optionally mathematical transformations of these quantities, for example, products or ratios. The controller then produces an output vector of future doses of administered pharmacologic agents, with the functional mapping (the controller function) between the inputs and outputs being derived by Dose Optimizer in the MPC scheme, as described above. In some embodiments, the preferred optimization technique to be used by the Dose Optimizer is Q-Learning, a Reinforcement Learning method that mimics trial-and-error skill acquisition by humans. In some embodiments, the controller function can be optionally represented by a set of decision rules, making the dosing regimen transparent to the user.

In some embodiments of the presently-disclosed subject matter, an exemplary system for personalized dosing of a pharmacologic agent can be provided as decision support software, such as a standalone software installed on a standard desktop PC, or as a web-based service for non-time-critical applications, for example for anemia or anti-coagulation management. In other embodiments, an exemplary system can be provided as dedicated hardware—for example, based on Digital Signal Processor or Application Specific Integrated Circuit—for time critical applications, for example for type I diabetes control or anesthesia control.

Turning now to FIG. 3, FIG. 3 shows an exemplary method 300 for personalized dosing of pharmacologic agents, such as the aforementioned decision support software, including the steps of: S302 deriving a plurality of dosing regimen functions that map physiologic response to pharmacologic agent dose from a corresponding plurality of dose-response models; S304 determining at each of a plurality of dosing steps a plurality of dosing recommendations that are specific to the respective dose-response models; S306 determining a response profile in response to receiving Response Indices of a subject; and S308 determining a recommended pharmacologic agent dose for the subject computed as a combination of the plurality of dosing recommendations weighted by degrees of matching computed using fuzzy sets and the response profile.

In the embodiments described herein, the aforementioned steps are implemented via a processing device, as described above, executing appropriate program modules of computer executable instructions stored on appropriate data storage device.

In some embodiments, the step S304, determining a plurality of dosing recommendations, is performed in response to receiving: data indicating a physiological characteristic of a subject over time; data indicating a pharmacologic agent dose over time; and a target therapeutic response. Of course, if data indicating certain values over time is not available, such as at the beginning of a treatment process, a current value only will necessarily be the "value over time." Indeed, when the patient has not received the drug before (i.e., when a treatment process is being initiated) the "current dose value" will be zero.

Figure 4:
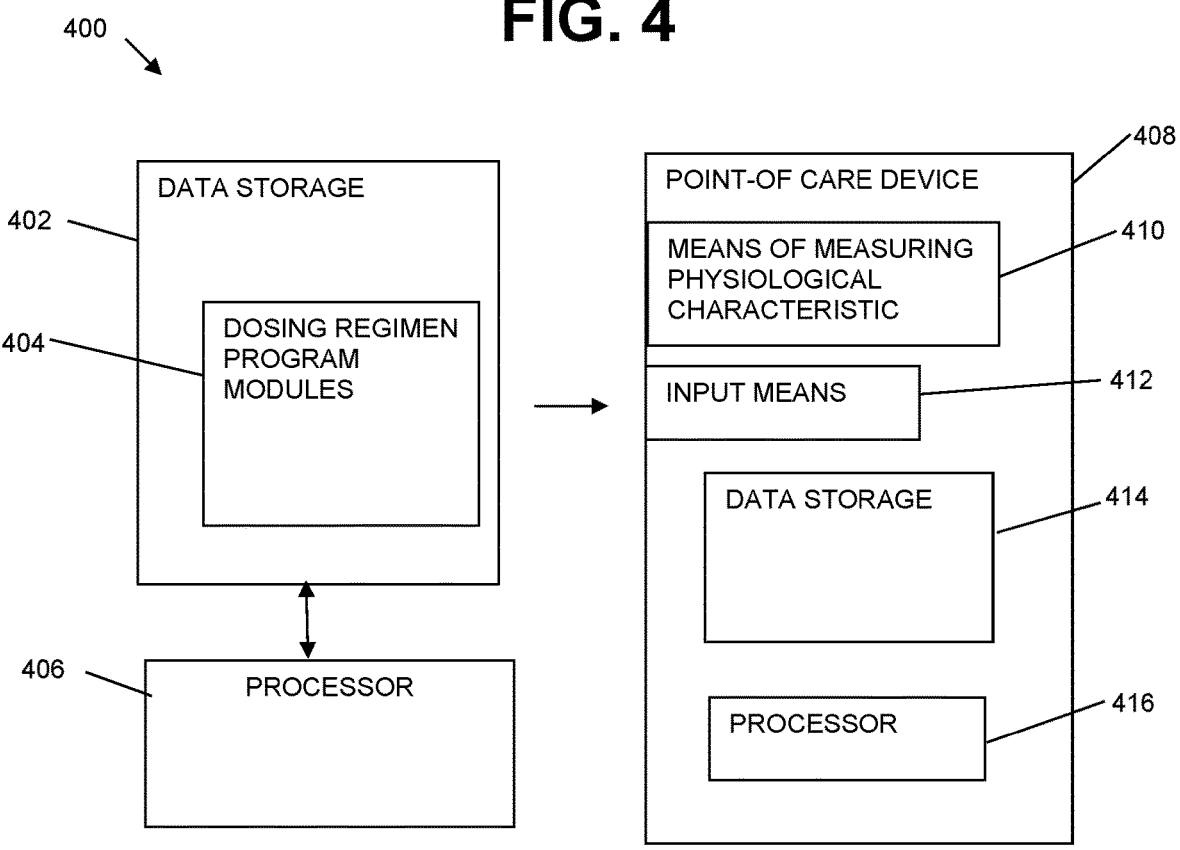
FIG. 4 is a block diagram of another embodiment of a system for personalized dosing of pharmacologic agents according to the invention.

FIG. 4 shows an exemplary system 400 for personalized dosing of pharmacologic agents. The exemplary system 400 includes a data storage device 402, dosing regimen program modules 404 stored on the data storage device 402, and a processing device 406 that uses the dosing regimen program modules to determine a plurality of dosing regimen functions that map physiologic response to pharmacologic agent dose from a corresponding plurality of dose-response models.

In some embodiments of the presently-disclosed subject matter, the exemplary system 400 also includes a point-of-care device 408. In some embodiments, and as shown in FIG. 4, the point-of-care device 408 includes a device 410 for measuring a current physiological characteristic value of a subject, an input device 412 for receiving a current pharmacologic agent dose value, a target therapeutic response value, and Response Indices of the subject, data storage device 414 for storing the dosing regimen functions, the current physiological characteristic value, the current pharmacologic agent dose value, the target therapeutic response value, prior physiological characteristic values, and prior pharmacologic agent dose values, and processing device 416 for executing computer executable instructions, as described below. It is noted that the device 410 for measuring a current physiological characteristic value of a subject, the input device 412, data storage device 414, and processing device 416 are shown together in FIG. 4 in the point-of-care device 408, but a routineer will recognize that such elements could be physically separated but still in data communication with each other via, for example, any form of wired or wireless communication, and even located vast distances from each other via, for example, the Internet. Such configurations are, of course, contemplated to be within the spirit and scope of the invention as disclosed herein.

In some embodiments, the point-of-care device 408 is a handheld dose calculator (e.g., a standalone dose calculator or a dose calculator including a device 410 for measuring a current physiological characteristic of a subject) built around a processing unit, such as Digital Signal Processors (DSP), Microcontrollers (uC), Programmable Logic Circuits (PLC), or Field-programmable Gate Arrays (FPGA), into which the processing steps of the dosing algorithm can be hard-coded. In such embodiments, the processing unit receives the input via peripheral devices, such as a keyboard or a touch pad that allows user inputs, or, optionally the processing unit receives input through built-in application-specific sensors including, but not limited to: optical or oxygen based Hb sensors such as those provided by HemoCue®/Quest Diagnostics, Angelholm, Sweden, or those provided by Massimo Corp., Irvine, CA; glucose readers such those provided by Accu-Chek®, Roche Diagnostics, Indianapolis, IN, or those provided by HemoCue®/Quest Diagnostics, Angelholm, Sweden; International Normalized Ratio (INR) readers such as Coagu-Chek®, Roche Diagnostics Inc., Indianapolis, IN or Pro-Time®, International Technidyne Corp., Edison, NJ. Regardless of the specific point-of-care device utilized, however, upon receipt of the input information, the processing device 416 then outputs the recommended dose and, optionally, other information, such as physiologic response over time, through a peripheral device such an LCD screen.

In other embodiments, the device 410 for measuring a current physiological characteristic value of a subject are more traditional means, such as obtaining a physical sample from a subject and analyzing it in a laboratory environment.

More specifically, the processing device 416 executes computer executable instructions for: determining a physiological characteristic value of the subject over time using the current physiological characteristic value and the prior physiological characteristic values; determining a pharmacologic agent dose over time value using the current pharmacologic agent dose value and the prior pharmacologic agent dose values; determining a plurality of dosing recommendations that are specific to the respective dose-response models using the dose regimen functions, the physiological characteristic value of the subject over time, the pharmacologic agent dose over time, and the target therapeutic response value; determining a response profile using the Response Indices of the subject; and determining a recommended pharmacologic agent dose for the subject computed as a combination of the plurality of dosing recommendations weighted by degrees of matching computed using fuzzy sets and the response profile. For example, in some embodiments that make use of the presently-disclosed system and method for personalized dosing of insulin, the processing device 416 can be built into an insulin pump such that the processing device 416 receives physiologic data from a continuous glucose monitor (e.g., such as those provided by Dexcom, Inc., San Diego, CA), stores the data in memory, and sends the recommended insulin doss to an attached insulin pump before storing that dose in memory as well.

As noted above, in some embodiments of the presently-disclosed subject matter, the methods and systems for personalized dosing of a pharmacologic agent can be precisely tailored for a particular pharmacologic agent, a particular disease condition, and/or a particular physiological characteristic value affected by that pharmacologic agent.

Figure 5:
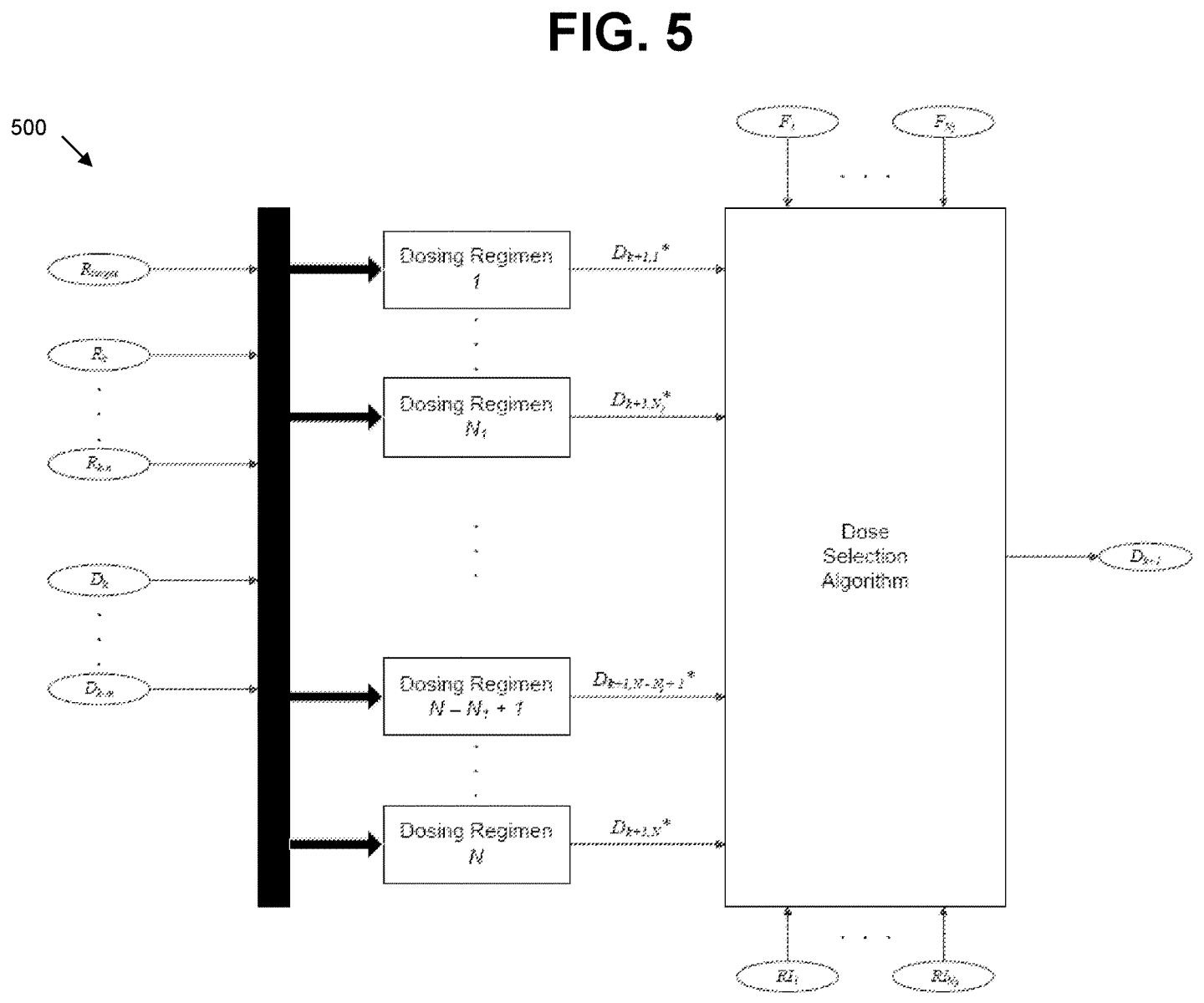

Turning now to FIG. 5, FIG. 5 is a schematic overview of an exemplary embodiment of a system 500 for personalized dosing of a particular pharmacologic agent. Not shown, but understood, are a data storage device for storing data and program instructions, a processing device, and an input device.

As shown in FIG. 5, in the system 500, the input device receives a $R_{target}$ value (target response(s) value), $R_k$ and $R_{k-n}$ values (measured physiologic response(s) value(s) over time that is computed from physiologic response data over time using lowess smoothing or another smoothing algorithm), and $D_k$ and $D_{k-m}$ values (past prescribed dose sets of the particular pharmacologic agents). Also shown are four dosing regimen program modules (Dosing Regimen 1, Dosing Regimen $N_1$, Dosing Regimen $N-N_{1+1}$, and Dosing Regimen N), which are understood to be stored in the data storage device. The dosing regimen program modules include instructions for causing the processing device to determine a new prescribed dose set $(D_{k+1,1}, \ldots D_{k+1,N})$ that is specific to each of the dosing regimen program modules and is specific to pharmacologic agent sensitivity profiles, as described in detail below. Lastly, shown is a dosing selection algorithm module, which is also understood to be stored in the data storage device. The dosing selection algorithm module, which is also described in detail below, includes instructions for causing the processing device to determine a $D_{k+1}$ value (recommended pharmacologic agent dose or new prescribed dose set) in response to certain Response Indices ($RI_1 \ldots RI_{N3}$) and Monitoring Frequencies ($F_1 \ldots F_{N2}$).

Figure 6:
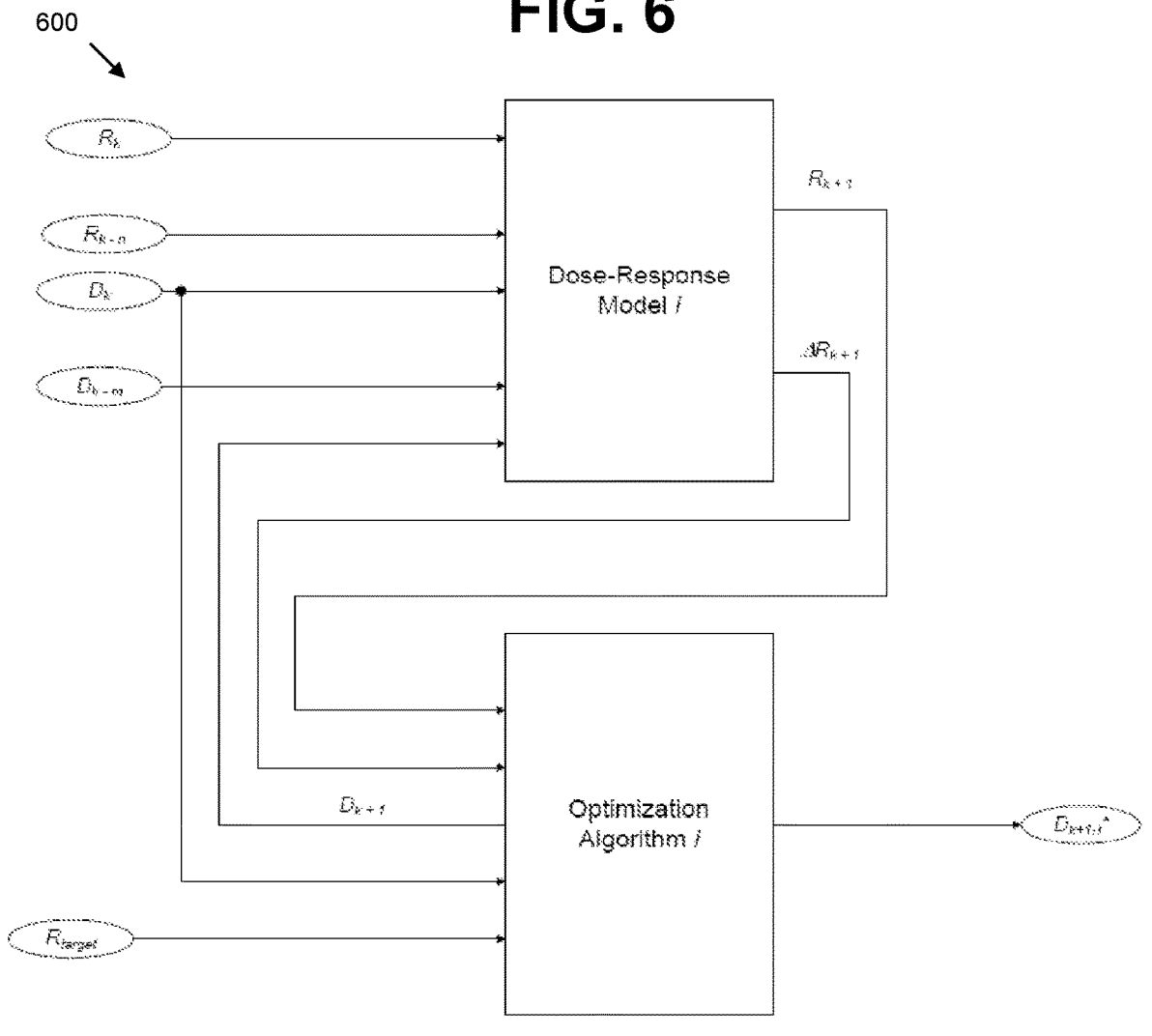
FIG. 6 is a schematic diagram of an exemplary dosing regimen program module.

Turning now to FIG. 6, FIG. 6 is a schematic view of an exemplary dosing regimen program module 600 for the exemplary system 500 of FIG. 5. As shown in FIG. 6, each of the dosing regimen program modules includes: a dose-response model module for causing the processing device to determine a $R_{k+1}$ value and a $\Delta R_{k+1}$ value (i.e., a predicted response) for a subject with a respective pharmacologic agent sensitivity profile based on the $R_k$ value, the $\Delta R_{k-n}$ value, and a proposed $D_{k+1}$ value; and an optimization algorithm module for causing the processing device to determine the optimal value $D_{k+1,i}*$ value using the $R_{target}$ value, and given the $R_{k+1}$ value and the $\Delta R_{K+1}$ value, and then iteratively providing the proposed $D_{k+1}$ value to the dose-response module and re-determining the proposed $D_{k+1}$ value until the proposed $D_{k+1}$ values converge to the optimal value $D_{k+1,i}*$, which is the value at which the objective function provided below in Equation (2) or (3) achieves minimum subject to optimization constraints.

In the exemplary dosing regimen program module 600, the dose-response model is substantially related to the function:

$$R_{k+1} = F(R_k, \ldots, R_{k-n}, D_{k+1}, D_k, \ldots, D_{k-m}, \theta_i) \qquad (1)$$

where:
F—linear or nonlinear function (mapping) describing the relationship between:
    measured physiologic response(s) over time: $R_k, \ldots, R_{k-n}$
    past prescribed dose sets of pharmacologic agent(s): $D_k, \ldots, D_{k-m}$
    new prescribed dose set of pharmacologic agent(s): $D_{k+1}$
    and
    predicted physiologic response(s) $R_{k+1}$
    given parameter vector $\theta_i=[\theta_1, \ldots, \theta_p]$ characterizing sensitivity profile i,
    where p is the number of response parameters; and
wherein the optimization algorithm is substantially according to the objective function:

$$D_i*(k+1) = \text{argmax} \; OFV(R_{target}, R(k), R_p(k+1), \qquad (2)$$

$$\ldots, R_p(k+H_p), D_{max}, D(k), D(k+1), \ldots, D(k+H_c))$$

-continued or $$D_i*(k+1) = \text{argmin} \; OFV(R_{target}, R(k), R_p(k+1), \qquad (3)$$

$$\ldots, R_p(k+H_p), D_{max}, D(k), D(k+1), \ldots, D(k+H_c))$$

subject to constraints:

$D_{min} \leq D \leq D_{max}$ $R_{min} \leq R \leq R_{max}$ $\Delta R_{min} \leq \Delta R \leq \Delta R_{max}$ where:
    $D_{min}$—minimum dose(s);
    $D_{max}$—maximum dose(s);
    $R_{min}$—minimum value(s) of physiologic response(s);
    $R_{max}$—maximum value(s) of physiologic response(s);
    $\Delta R_{min}$—minimum value of rate(s) of change of physiologic response(s); and
    $\Delta R_{max}$—maximum value of rate(s) of change of physiologic response(s)
    are design parameters specified by the user, and
    where OFV is an objective function value as described herein above.

In Equation (1) above, Function F can be an equation or a set of equations derived from first-principles, i.e. knowledge of physiology (white-box model), where parameters $\theta_i$ have a physiologic interpretation. In other embodiments, function F can be an equation or a set of equations derived from simplified first-principles and numerical data (grey-box model), such that $\theta_i$ may have a mechanistic but not necessarily physiologic interpretation. In further embodiments, function F can be an equation or a set of equations derived purely from numerical data (black-box model), where parameters $\theta_i$ do not have a mechanistic or a physiologic interpretation.

Figure 7:
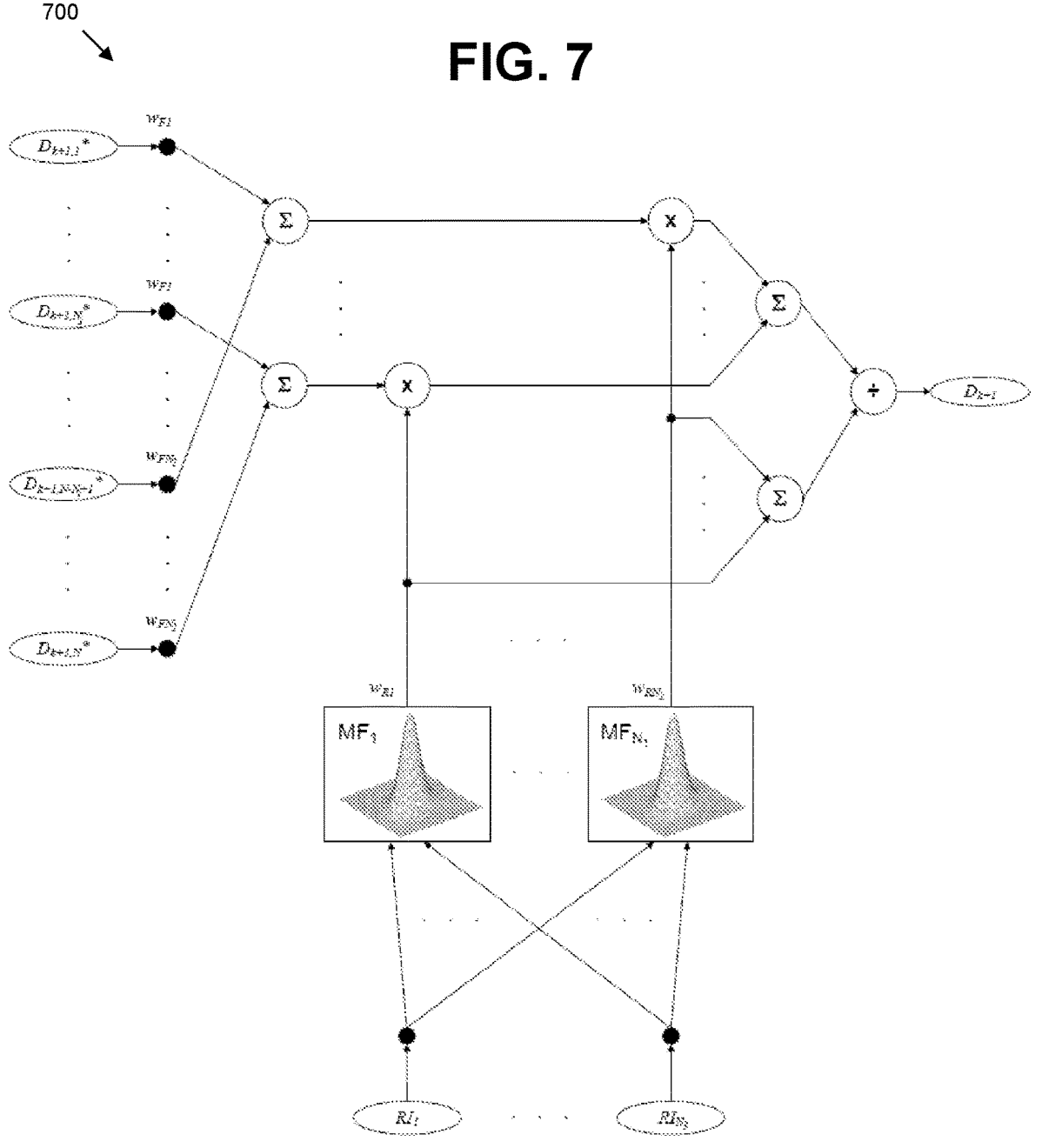
FIG. 7 is a schematic diagram of an exemplary dose selection algorithm module.

Turning now to FIG. 7, FIG. 7 is a schematic diagram of an exemplary dose selection algorithm module 700 for the exemplary system 500 of FIG. 5. As shown in FIG. 7, in the exemplary dose selection algorithm module 700 there are 4 dosing regimens, or new prescribed dose sets specific to pharmacologic agent sensitivity profiles and monitoring frequencies, $(D_{k+1,1}*, D_{k+1,N1}*, D_{k+1,N1+1}*, D_{k+1,N}*)$ and the dosing selection algorithm module determines the $D_{k+1}$ value by multiplying $D_{k+1,1}*, \ldots D_{k+1,N}*$ by the frequency weights $W_{F1} \ldots W_{F2}$ where:
    $w_{Fi}=1$ if current monitoring frequency$=F_i$
    $w_{Fi}=0$ otherwise $W_{F1}$ By multiplying the new prescribed dose sets by the monitoring frequency weights, only dose sets recommended for current monitoring frequency are selected. These dose sets are then weighted averaged by pharmacologic agent sensitivity profile weights $w_{R1} \ldots w_{RN1}$ calculated from response indices $RI_1 \ldots RI_{N3}$ using fuzzy membership function $MF_1 \ldots MF_{N1}$, where:
    $RI_1 \ldots RI_{N3}$ response indices $1 \ldots N_3$
    $MF_1 \ldots MF_{N1}$ $N_3$-dimensional fuzzy membership functions $1 \ldots N_1$ map the response indices $RI_1 \ldots RI_{N3}$ to weights $w_{R1} \ldots w_{RN1}$ which represent similarity between the subject and pharmacologic agent sensitivity profile $1 \ldots N_1$ $w_{R1}=1$ if there is perfect matching between ($RI_1$ . . . $RI_{N3}$) and sensitivity profile i $0<w_{Ri}<1$ if there is partial matching between ($RI_1$ . . . $RI_{N3}$) and sensitivity profile i $w_{Ri}=0$ if there is no matching between ($RI_1$ . . . $RI_{N3}$) and sensitivity profile I;

In some embodiments, the parameters of membership functions $MF_1$ . . . $MF_{N1}$ above are specified a priori by the designer based on expert knowledge and data relating specific values of $RI_1$ . . . $RI_{N3}$ to pharmacologic agent sensitivity profile 1 . . . $N_1$.

As one exemplary embodiment of a personalized system and method for dosing a particular pharmacologic agent in accordance with the presently-disclosed subject matter, in some embodiments, a system and method for personalized dosing of an erythropoietic stimulating agent is provided for the treatment and/or management of anemia in a subject. The terms "erythropoietic agent," "erythropoietic stimulating agent," "erythropoiesis stimulating agents," "Epo," or "ESA(s)" are used interchangeably herein to refer to agents that are capable of stimulating red blood cell production. As such, the term Epo is inclusive of erythropoietin, but is also inclusive, in some embodiments, of iron or iron attached to various carrier proteins, as well as various pharmaceutical preparations of erythropoietin including, but not limited to, Epoetin, Procrit or Epogen or Eprex or ReliPoietin or Epokine or Shanpoietin (epoetin-alpha), Epoetin-alpha, neo-Recormon or Betapoietin (epoetin-beta), Epoetin-beta, Aranesp (darbepoetin), Darbopoetin alfa, Mircera (methoxy polyethylene glycol-epoetin beta), Methoxy Polyethylene Glycol-Epoetin beta, Dynepo (Epoetin delta), Epoetin delta, Hematide (peginesatide) and formulations of pharmaceutical preparations such as HIF PHI (HIF prolyl hydroxylase inihibor FG-2216 by FibroGen, Inc.) that effect the biological activity of prolyl hydroxylation including, but not limited to, hypoxia inducible factor alpha or beta subunits.

Figure 8:
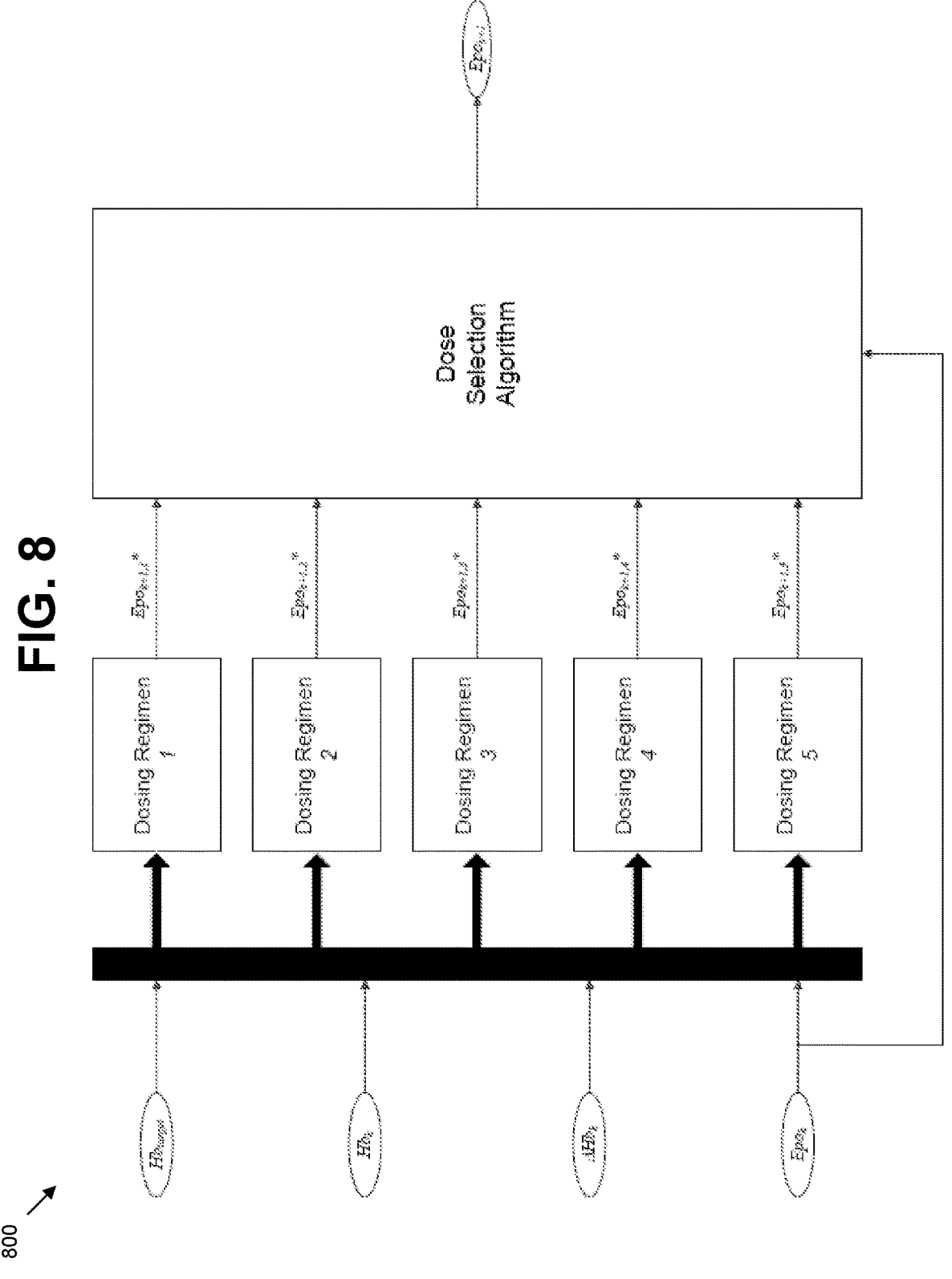
FIG. 8 is a schematic overview of an exemplary embodiment of a system for personalized dosing of an erythropoietic stimulating agent (Epo) for managing anemia.

FIG. 8 is a schematic overview of an exemplary embodiment of a system 800 for personalized dosing of an erythropoietic stimulating agent (Epo) for managing anemia. Also not shown, but understood in this embodiment, are data storage device for storing data and program instructions; a processing device; and an input device.

As shown in FIG. 8, in the system 800, the input device receives a $Hb_{target}$ value (target hemoglobin level (g/dL)), a $Hb_k$ value (Hb level (g/dL) computed from Hb data over time using lowess smoothing or another suitable smoothing method with a 28 day window), a $\Delta Hb_k$ value (Hb rate of change (g/dL per day) computed from Hb data over time using lowess smoothing or another suitable smoothing method with a 28 day window), and an $Epo_k$ value, which corresponds to the Epo dose previously received (Epo dose received (e.g., 1000 Units per week) or computed from Epo data over time as an average weekly Epo dose received over the preceding 28 days, if the previously-prescribed dose is not available. Also shown are five dosing regimen program modules ("i"=5), which are understood to be stored in the data storage device. The dosing regimen program modules include instructions for causing the processing device to determine an $Epo_{k+1,i}$ value (recommended Epo dose (e.g., 1000 Units per week) for each of the "i" dosing regimens, the details of which are described below. Lastly, shown is a dosing selection algorithm module, which is also understood to be stored in the data storage device. The dosing selection algorithm module, which is also described in detail below, includes instructions for causing the processing device to determine an $Epo_{k+1}$ value (recommended Epo dose (e.g., 1000 Units per week)).

Figure 9:
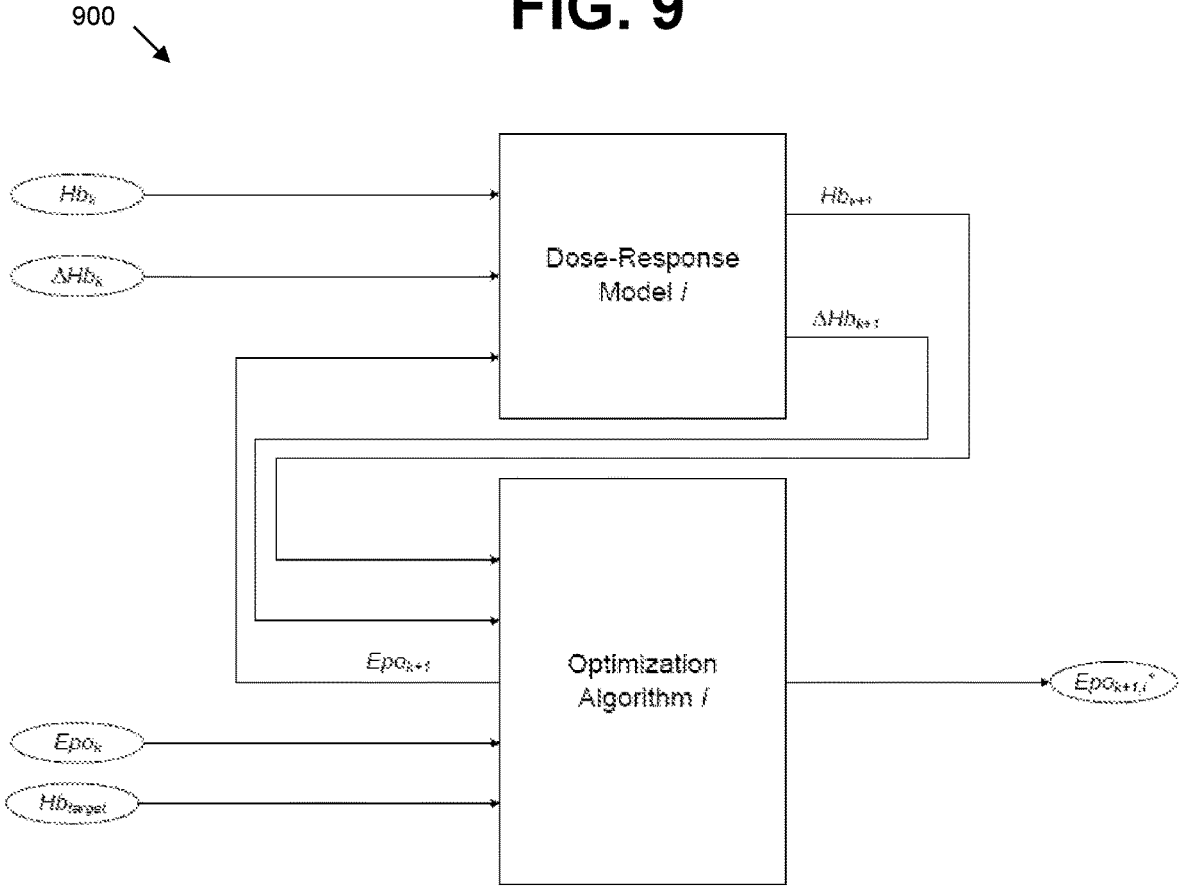
FIG. 9 is a schematic view of an exemplary dosing regimen program module for the exemplary system of FIG. 8.

Turning now to FIG. 9, FIG. 9 is a schematic view of an exemplary dosing regimen program module 900 for the exemplary system 800 of FIG. 8. As shown in FIG. 9, each of the "i" dosing regimen program modules includes: a dose-response model module for causing the processing device to determine a $Hb_{k+1}$ value and a $\Delta Hb_{k+1}$ value (i.e., a predicted response) for a subject with a respective Epo sensitivity profile based on the $Hb_k$ value, the $\Delta Hb_k$ value, and a proposed $Epo_{k+1}$ value; and an optimization algorithm module for causing the processing device to determine the optimal value $Epo_{k+1,i}^*$ value using the $Hb_{target}$ value, and given the $Epo_k$ value, the $Hb_{k+1}$ value and the $\Delta Hb_{k+1}$ value, and then iteratively providing the proposed $Epo_{k+1}$ value to the dose-response module and re-determining the proposed $Epo_{k+1}$ value until the proposed $Epo_{k+1}$ values converge to the optimal value $Epo_{k+1,i}^*$, which is the value at which the objective function provided below in Equation (6) achieves minimum subject to optimization constraints.

In the exemplary dosing regimen program module 900, the dose-response model is substantially according to the function:

$$\begin{bmatrix} \dfrac{dHb}{dt} \\ \dfrac{d\Delta Hb}{dt} \end{bmatrix} = \begin{bmatrix} \dfrac{-2}{T_i} & \dfrac{1}{T_i^2} \\ 1 & 0 \end{bmatrix} \begin{bmatrix} Hb \\ \Delta Hb \end{bmatrix} + \begin{bmatrix} \dfrac{K_i}{T_i^2} \\ 0 \end{bmatrix} Epo \tag{4}$$

where:

$K_i$—erythropoietic response (1,000 Units Epo per 1 g/dL Hb change);

$T_i$—time constant;

Epo—dose (1,000 Units);

Hb—hemoglobin level (g/dL);

$\Delta Hb$—hemoglobin rate of change (g/dL per day);

where:

$K_i$ and $T_i$ are mechanistic parameters describing sensitivity (K) and dynamics (T) of the red blood cell production process;

K is physiologically related to red cell production rate;

T is physiologically related to mean red blood cell lifespan; and where:

a discrete time grey-box model describing Hb response to Epo can be derived by sampling Equation (4) every $T_s$ days $$\begin{bmatrix} Hb_{k+1} \\ \Delta Hb_{k+1} \end{bmatrix} = \begin{bmatrix} \theta_{i,1} & \theta_{i,2} \\ \theta_{i,2} & \theta_{i,4} \end{bmatrix} \begin{bmatrix} Hb_k \\ \Delta Hb_k \end{bmatrix} + \begin{bmatrix} \theta_{i,5} \\ \theta_{i,6} \end{bmatrix} Epo_{k+1} \tag{5}$$

where:

k—time step $\theta_i=[\theta_{i,1}, \theta_{i,2}, \theta_{i,3}, \theta_{i,4}, \theta_{i,5}, \theta_{i,6}]$—parameter vector derived from $K_i$ and $T_i$ by sampling Equation (4) every $T_s$ days; and wherein the optimization algorithm is substantially according to the objective function:

$$OFV = \sum_{k_p=1}^{H_p} \left( Hb_{target} - Hb_{k_p} \right)^2 + \lambda_i \sum_{k_c=1}^{H_c} \Delta Epo_{k_c}^2 \tag{6}$$

where:

$k_p$, $k_c$—time steps (weeks);

$H_p$—prediction horizon (weeks);

$H_c$—control horizon (weeks);

$\lambda_i$—dose change suppression (non-dimensional);

$Hb_{kp}$—hemoglobin at step $k_p$;

$\Delta Epo_{kc}$—change in dose from step $k_{c-1}$ to $k_c$; and subject to constraints:

$$0 \leq Epo \leq 90{,}000 \text{ units per week}$$

$$0 \leq Hb \leq 20 \text{ g/dL}$$

$$-0.5 < \Delta Hb < 0.5 \text{ g/dL per week}$$

where: $\Delta Hb = Hb_{kp} - Hb_{kp-1}$.

Equation (4) above is a continuous time equation that describes the dynamic behavior of Hb and the Hb rate of change ($\Delta Hb$) in response to an Epo dose, given a fixed Epo sensitivity profile i described by two parameters: Ki, or the erythropoietic response which represents the magnitude of Hb increase (decrease) in steady-state after the Epo dose has been increased (or decreased) by 1,000 Units; and Ti, or the time constant that is mathematically related to the time required for Hb to achieve the steady-state after the Epo dose has been increased (or decreased). In some embodiments, Equation (1) is used as the Dose-Response Model to calculate the $Hb_{k+1}$ and $\Delta Hb_{k+1}$ values from the $Hb_k$ and $\Delta Hb_k$, and to also calculate the $Epo_k$ value.

Equation (6), on the other hand, describes the objective function to be minimized by $Epo_{k+1,i}^*$. The first right-hand-side term of this equation sums the squared difference between $Hb_{target}$ and Hb predicted by the Dose-Response Model (Equation 1) at time steps kp, where kp changes from 1 through prediction horizon Hp. The second right-hand term sums the squared amounts of Epo dose adjustments at time step $k_c$, where $k_c$ changes from 1 through control horizon $H_c$. In this regard, the first term thereby represents the tracking properties of the controller, i.e. how well the measured Hb is maintained close to target, while the second term represents robustness of the controller, i.e. how well the controller ignores random changes in measured Hb. The balance between tracking and robustness is determined by the parameter $\lambda_i$.

In one embodiment of the exemplary dosing regimen program module 900, the following parameters are applied:

| Dose Response Models: $2_{nd}$ order with repeated poles | | |
|---|---|---|
| Sampling time | $T_s = 7$ | (days) |
| Dose Response Model 1 | $K_1 = 0.03$ | $T_1 = 12$ |
| Dose Response Model 2 | $K_2 = 0.05$ | $T_2 = 12$ |
| Dose Response Model 3 | $K_3 = 0.10$ | $T_3 = 12$ |
| Dose Response Model 4 | $K_4 = 0.25$ | $T_4 = 12$ |
| Dose Response Model 5 | $K_5 = 1.00$ | $T_5 = 12$ |

| Optimization Method: Quadratic Programming | | |
|---|---|---|
| Prediction horizon | $H_p = 17$ | (weeks) |
| Control horizon | $H_c = 1$ | (weeks) |
| Dose Change Suppression 1 | $\lambda_1 = 0.1$ | |
| Dose Change Suppression 2 | $\lambda_2 = 0.3$ | |
| Dose Change Suppression 3 | $\lambda_3 = 0.5$ | |
| Dose Change Suppression 4 | $\lambda_4 = 1.0$ | |
| Dose Change Suppression 5 | $\lambda_5 = 2.0$ | |

In the embodiment of the exemplary dosing regimen program module whose parameters are shown above, the sampling time of 7 days was selected based on an optimal frequency of Hb observation, while the values of the erythropoietic response parameter (K) for Dose-Response Models 1 through 5 were selected to cover a maximum possible range of Epo doses that can be given to a subject, as regulated by NKF-K/DOQI guidelines and the product label. The time constant parameter for all the models was selected to represent the average RBC lifespan typical for the hemodialysis patient population of 90 days. The controller parameters ($H_p$, $H_c$, and $\lambda_1$ through $\lambda_5$) were optimized to achieve time to reach Hb steady-state not greater than 12 weeks in response to a 1,000 Unit change in Epo dose and to miminize Epo dose changes in response to random noise in Hb measurement. Of course, for a particular application, the dosing regimen program module parameters can further be adapted or changed as desired without departing from the spirit and scope of the subject matter described herein.

Figure 10:
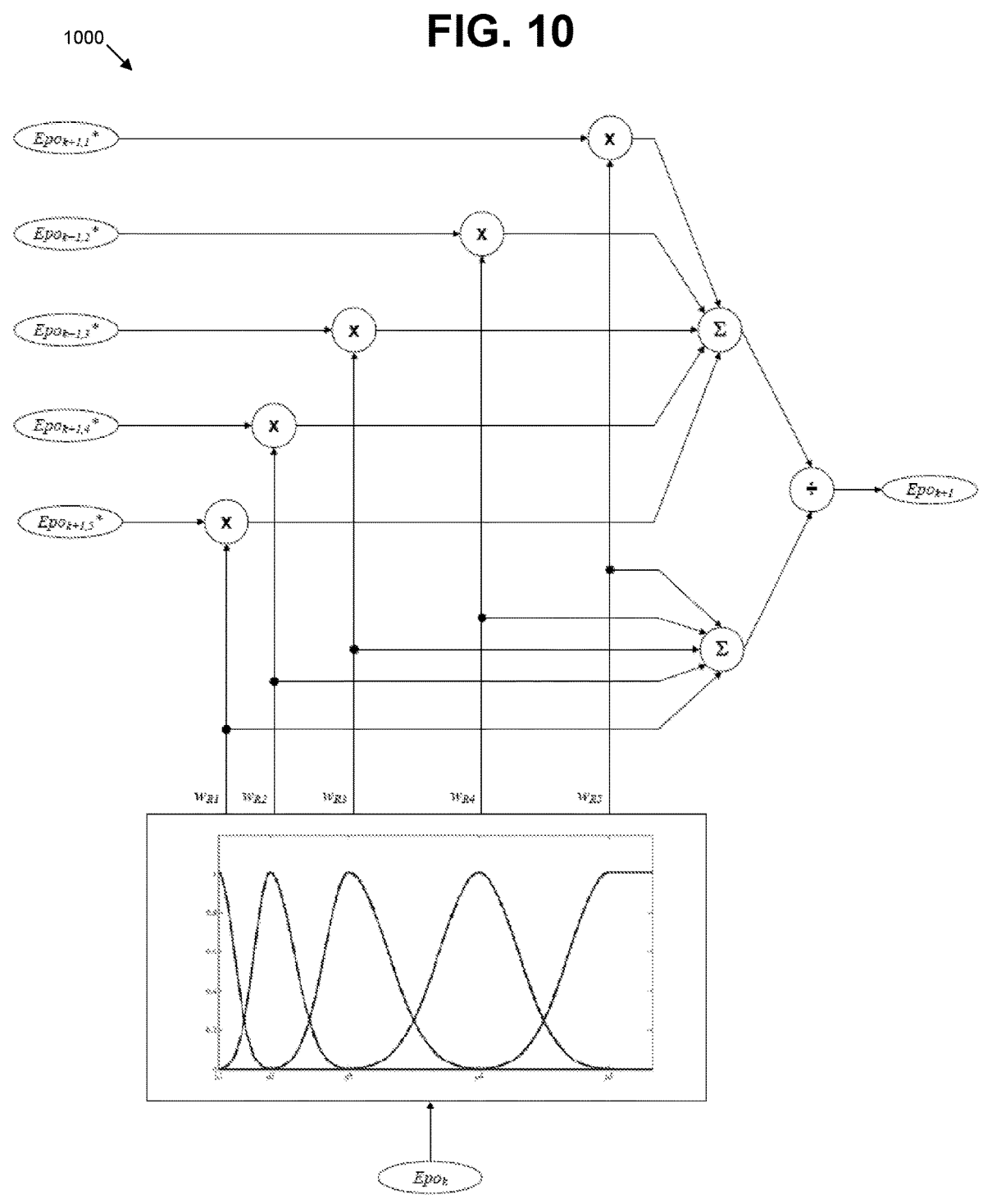
FIG. 10 is a schematic diagram of an exemplary dose selection algorithm module for the exemplary system of FIG. 8.

FIG. 10 is a schematic diagram of an exemplary dose selection algorithm module 1000 for the exemplary system 800 of FIG. 8. As shown in FIG. 10, in the exemplary dose selection algorithm module 1000 there are 5 dosing regimens ("i"=5) and the dosing selection algorithm module determines the $Epo_{next}$ value substantially according to the equation (function):

$$Epo_{k+1} = \frac{\begin{array}{l} w_{R1}Epo_{k+1,1}^* + w_{R2}Epo_{k+1,2}^* + w_{R3}Epo_{k+1,3}^* + \\ w_{R4}Epo_{k+1,4}^* + w_{R5}Epo_{k+1,5}^* \end{array}}{w_{R1} + w_{R2} + w_{R3} + w_{R4} + w_{R5}}. \quad (7)$$

The weighting values are fuzzy membership functions according to the following:

| | | | |
|---|---|---|---|
| $w_{R1} = f_{MF}(Epo_k, \mu_1, s_{1l}, s_{1r})$ | $\mu_1 = 0$ | $s_{1l} = 1.0$ | $s_{1r} = 0.9^*(Hb_{target} - Hb_0)$ |
| $w_{R2} = f_{MF}(Epo_k, \mu_2, s_{2l}, s_{2r})$ | $\mu_2 = 3^*(Hb_{target} - Hb_0)$ | $s_{2l} = s_{1r}$ | $s_{2r} = 1.35^*(Hb_{target} - Hb_0)$ |
| $w_{R3} = f_{MF}(Epo_k, \mu_3, s_{3l}, s_{3r})$ | $\mu_3 = 7.5^*(Hb_{target} - Hb_0)$ | $s_{3l} = s_{2r}$ | $s_{3r} = 2.25^*(Hb_{target} - Hb_0)$ |
| $w_{R4} = f_{MF}(Epo_k, \mu_4, s_{4l}, s_{4r})$ | $\mu_4 = 15^*(Hb_{target} - Hb_0)$ | $s_{4l} = s_{3r}$ | $s_{4r} = s_{4l}$ |
| $w_{R5} = f_{MF}(Epo_k, \mu_5, s_{5l}, s_{5r})$ | $\mu_5 = 22.5^*(Hb_{target} - Hb_0)$ | $s_{5l} = s_{4r}$ | $s_{5r} = 100.0$ | where $f_{MF}$ is a fuzzy membership function substantially according to the equation:

$$f_{MF}(x, \mu, s_t, s_r) = \begin{cases} \exp\left(-\dfrac{(x-\mu)^2}{s_i^2}\right) & x < \mu \\ 1 & x = \mu \\ \exp\left(-\dfrac{(x-\mu)^2}{s_r^2}\right) & x > \mu \end{cases} \quad (8)$$

and $Hb_0$ is baseline hemoglobin, which is the hemoglobin level before first administration of Epo.

In Equation (8) above, the parameter u represents the center of the fuzzy membership function and the parameters $s_1$ and $s_r$ represent the left and right spread of the membership function, respectively. In some embodiments, the centers (i.e., where the membership achieves the maximum value of 1.0) were chosen to represent the most typical Epo dose value received by the subjects belonging to the specific sensitivity profile, while the spreads were chosen to achieve the overlap between the neighboring membership functions at the value of 0.25.

Figure 11:
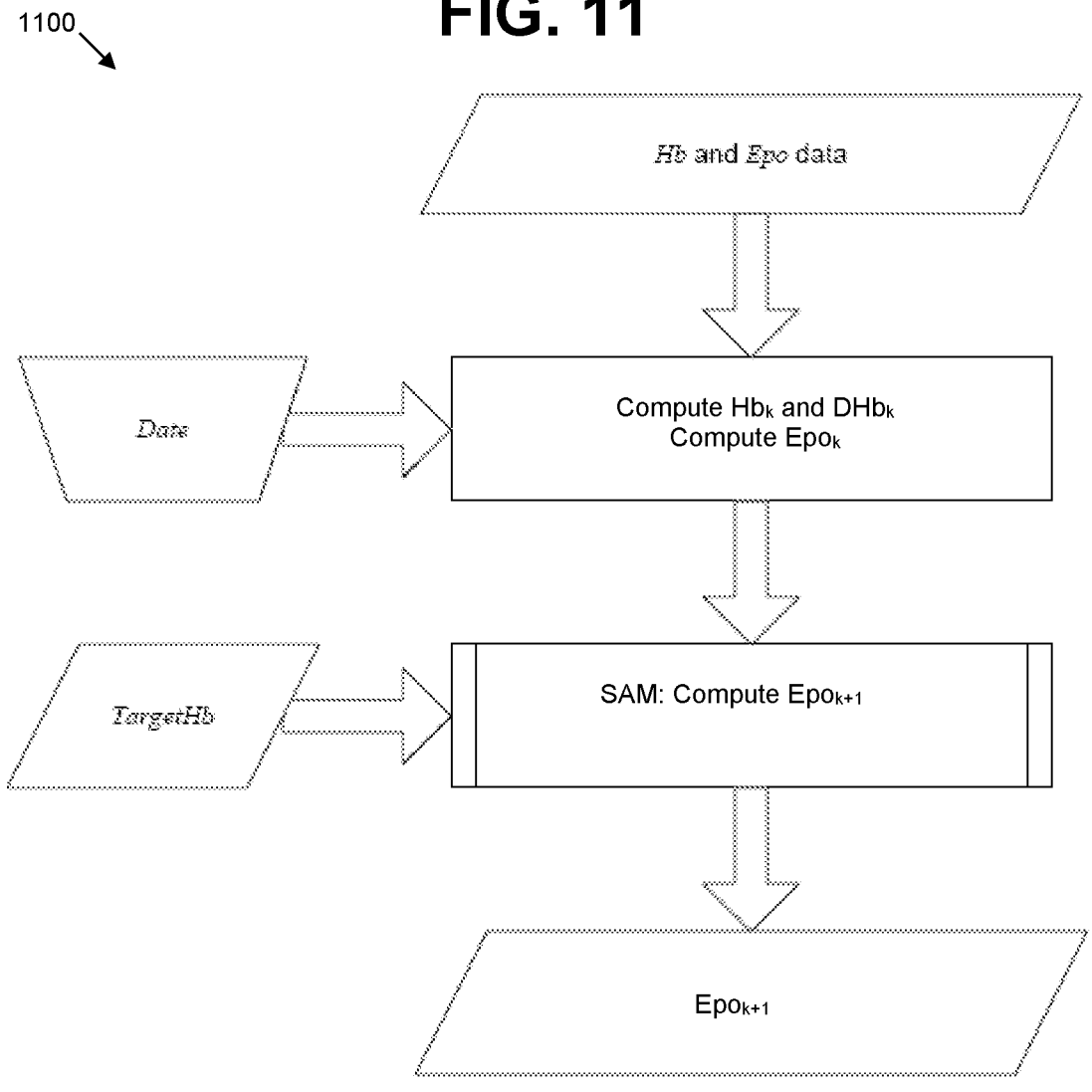
FIG. 11 is a flowchart of an exemplary method for personalized dosing of erythropoietic stimulating agents for managing anemia.

FIG. 11 is a flowchart of an exemplary method 1100 for personalized dosing of erythropoietic stimulating agents for managing anemia, according to the steps described in conjunction with the description of the exemplary system 800 (FIG. 8) for personalized dosing of erythropoietic stimulating agents for managing anemia. It is further noted though that a number of control methods can be used to derive dosing regimens. For example, it is anticipated that Reinforcement Learning methods could be used. Additionally, it is contemplated that, at every dosing step, each dosing regimen (function) can take in input information on physiologic response, pharmacologic agent, and the target therapeutic response and then produce its own dosing recommendation that is specific to its response profile to achieve the therapeutic target. In this regard, it is yet further contemplated that the systems and methods disclosed herein could be used for a number of pharmacologic agents and for the treatment and/or management of a number of diseases and disorders, including, but not limited to: immunosuppression management; type 1 diabetes management; type 2 diabetes management; other blood glucose control; iron management; hypertension management; gout treatment and management; anticoagulation management; and control of anesthesia. For example, it is contemplated that the systems and methods of the presently-disclosed subject matter can be used for insulin dosing where the inputs include blood glucose levels or levels over time and the target therapeutic response relates to a target blood glucose level or range. As further examples, it is contemplated that the systems and methods of the presently-disclosed subject matter can be used for: warfarin dosing where the inputs include an INR levels or levels over time and the target therapeutic response relates to a target INR level or range for a particular subject; heparin dosing wherein the inputs are thromboplastin time or clotting time and the target therapeutic response relates to a target thromboplastin time or clotting time; enoxaparin dosing where the inputs include an anti-factor 10A level and the target therapeutic response relates to a target anti-factor 10A level; injectable and oral iron supplement dosing wherein the inputs are serum iron levels, serum ferritin levels, or transferrin saturation and where the target therapeutic response relates to a target serum iron level, serum ferritin level, or transferrin saturation; hypertensive agents dosing where the inputs include blood pressure levels and the target therapeutic response relates to a target blood pressure level or range; immunosuppressive agent dosing wherein the inputs include plasma pharmacologic agent levels, rejection rates, and/or functional measures of immunity and the target therapeutic response relates to a target plasma pharmacologic agent levels, rejection rates, and/or functional measures of immunity; and xanthine oxidase inhibitor dosing where the inputs include uric acid levels or ranges and the target therapeutic response relates to target uric acid levels, such as target uric acid levels necessary for the treatment of gout.

With further respect to the system and method for personalized dosing of an erythropoietic stimulating agent and for management of anemia described herein, in some embodiments, the systems and methods can make use of software (e.g., a standalone program or remote web service), for non-time critical applications such as anemia management where the physiologic response (Hb values) are obtained electronically from electronic health records of subjects whose hemoglobin values have been inputted into the electronic records by a centralized laboratory that analyzed the initial blood sample obtained from the subject. In other embodiments, however, and as described above, hardware, such as point-of-care devices, can be utilized and the subject can self-administer the pharmacologic agent.

With respect to the presently-disclosed subject matter, a preferred subject is a vertebrate subject. A preferred vertebrate is warm-blooded; a preferred warm-blooded vertebrate is a mammal. A preferred mammal is most preferably a human. As used herein, the term "subject" includes both human and animal subjects. Thus, veterinary therapeutic uses are provided in accordance with the presently-disclosed subject matter. As such, the presently-disclosed subject matter provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The presently-disclosed subject matter is further illustrated by the following specific but non-limiting examples. Some of the following examples may include compilations of data that are representative of data gathered at various times during the course of development and experimentation related to the presently-disclosed subject matter.

EXAMPLES

Example 1

Analysis of Hemoglobin Control and Cost Savings

To analyze the ability of the presently-disclosed system and method for personalized Epo dosing to control hemoglobin level, and the cost of administering Epo, a retrospective controlled clinical trial of the system and method for "smart anemia management" or "SAM"(n=68) versus a traditional algorithmic approach ("TAP") (n=66) was conducted in a dialysis facility for 6 months prior to the introduction of SAM to the 6 months after SAM and between TAP and SAM. The SAM program was implemented as a standalone program that read EPO dose and hemoglobin data from an electronic medical record. It then determined the best subject-specific future dose of EPO based on the model predictive control algorithm described herein above. The TAP was developed as an expert system based on the EPO package insert and KDOQI guidelines.

The target Hb was 11.0 g/dl in both groups, and the mean Hb and weekly EPO dose was measured.

Shown below in Table 1 are the mean plus or minus the standard deviation for Hb and mean weekly EPO dose for the period 6 months prior to and 6 months after the implewas observed to outperform Protocols 1 and 2 in terms of percent Hb within target range. Additionally, increasing intra-subject variability decreased percent Hb within target. Anemia management with SAM results in a 36% relative decrease in Epo dose compared to Protocol 1 and 2. Intra-subject variability did not significantly affect Epo utilization.

TABLE 2

| Intrapatient variability (g/dL) | Protocol 1 | | Protocol 2 | | SAM | |
|---|---|---|---|---|---|---|
| | % Hgb 10-12 | Mean Epo per Pt-wk | % Hgb 10-12 | Mean Epo per Pt-wk | % Hgb 10-12 | Mean Epo per Pt-wk |
| 0.0 | 68 | 11,200 | 50 | 11,500 | 74 | 7,300 |
| 0.5 | 54 | 10,400 | 44 | 12,000 | 67 | 7,300 |
| 1.0 | 40 | 9,800 | 33 | 13,000 | 48 | 7,100 | mentation of SAM. SAM was able to achieve the target Hb within the time course of the study while TAP was not. Decreasing the population mean Hb resulted in EPO sparing in both groups but SAM resulted in an additional EPO sparing of about 2,800 units per week. SAM also resulted in a 10% decrease in Hb variability as measured by Hb standard deviation. These results thus indicated that the prospective prediction of Hb response to EPO dosing with SAM was superior to an expert rule based technique used in the management of the anemia of end-stage renal disease. Specifically, it was observed that SAM exposed subjects to less EPO, better achieved the target Hb, and resulted in cost savings to dialysis units in the range of $1,100-$3,800/subject/year, depending on current EPO usage.

TABLE 1

| | Hb Before | Hb After | EPO Before | EPO After |
|---|---|---|---|---|
| TAP | 11.5 ± 0.93 | 11.3 ± 1.00 | 10,777 | 8,734 |
| SAM | 11.3 ± 0.9 | 11.0 ± 0.9 | 9,029 | 5,902 |

Example 2

Validation of System and Method for Anemia Management

To further assess the presently-disclosed system and method for managing anemia, the system and method for individualized Epo dosing or "SAM" was compared against two standard protocols through in silico simulation. Briefly, in this analysis, end-stage renal disease (ESRD) subjects were represented with a mathematical model of erythropoiesis relating weekly Hb to weekly Epo dose received. To account for inter-subject variation in Epo response, a pool of models was created with different (fixed) parameters including Epo sensitivity from 0.1 to 0.9 g/dL per 1,000 ESA Units per week. RBC lifespan between 60 and 120 days, body mass 50 to 150 kg, and baseline Hb 7 to 9 g/dL. Intra-subject Hb variability was represented by normally distributed random noise with zero mean and standard deviation 0.0 to 1.0 g/dL. All the simulation parameters other than Hb. Epo dose and body mass were not visible to SAM nor the benchmark protocols. Hb response was simulated over 12 months and used the following performance metrics: percent Hb levels within target range (10-12 g/dL), and mean ESA dose per subject-week.

The results of the comparison are shown in Table 2 below for three different levels of intra-subject variability. SAM

Example 3

Assessment of Computer-Aided Personalized Anemia Management

Figures 12, 13:
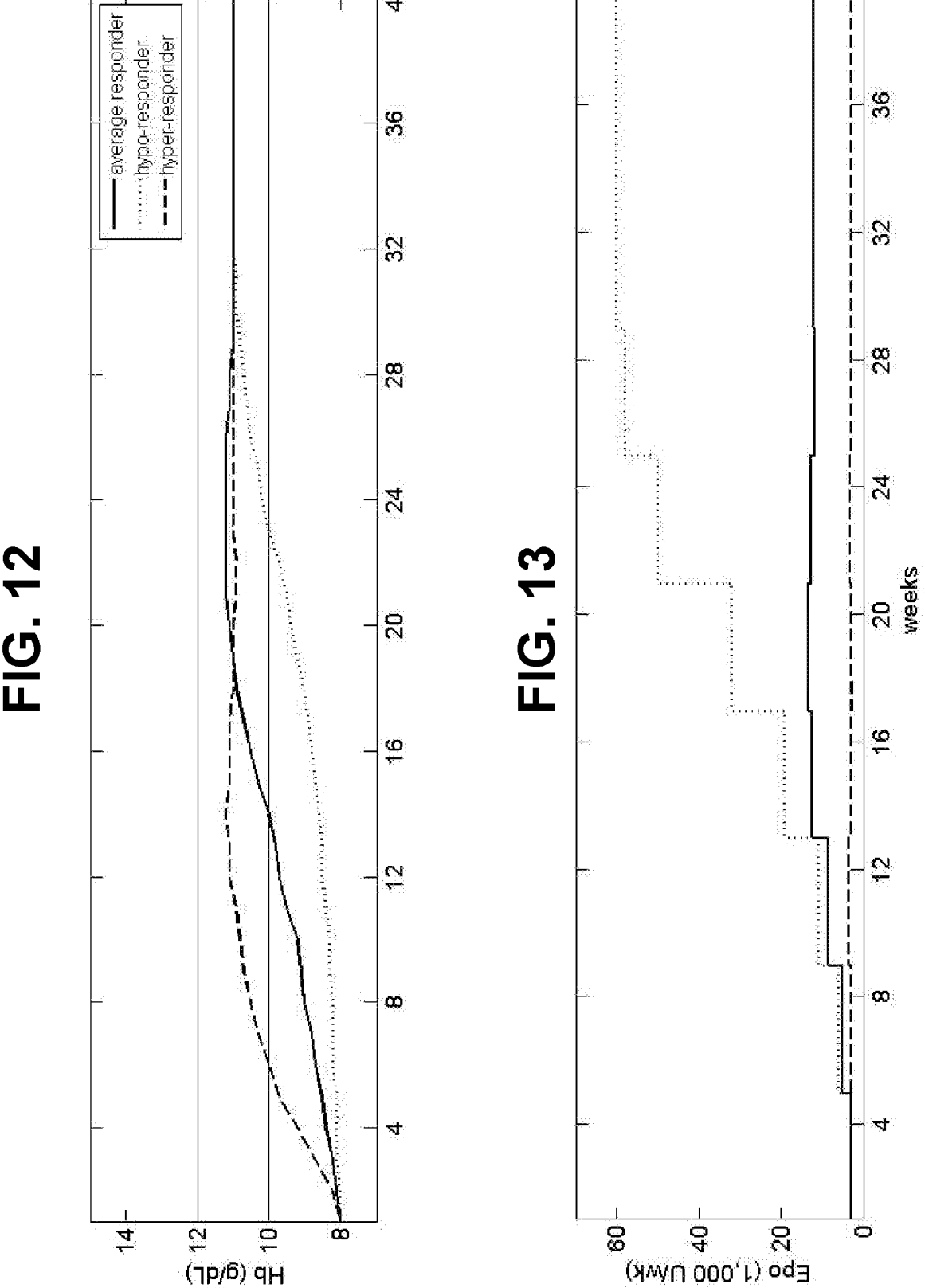
FIG. 12 is a graph showing the Hb response for three representative subject models that were analyzed using a system and method for smart anemia management of the invention.
FIG. 13 is a graph showing the Epo dose profile for the three representative subject models of FIG. 12.

To also assess the ability of the presently-disclosed computer-aided personalized anemia management systems and methods or "SAM" to effectively manage Epo dosing, additional in silico testing was performed. Briefly, in these additional experiments and using data from ESRD subjects receiving Epoetin alfa (Epo), three models representing typical pharmacodynamic (PD) Hemoglobin (Hb) response to Epo were developed: hypo-, average, and hyper-responder. PD characteristics were represented by erythropoietic sensitivity (0.05, 0.25, and 1.0 g/dL per 1000 U/wk) and average erythrocyte lifespan (60, 90, 120 days). Using the three response models, anemia management was simulated over a period of 37 weeks starting at baseline Hb=8 g/dL. SAM drove Hb from the baseline value to the target range (10-12 g/dL) for all three test subjects. The time to reach the target range was 23 (hypo-), 14 (average), and 7 (hyper-responder) weeks. The standard anemia management protocol used at the facility from which the data was obtained achieved the target Hb in 23 (hypo-) and 11 (average responder) weeks. For hyper-responder, the protocol resulted in Hb cycling and did not achieve a stable response. FIGS. 12 and 13 show the Hb response (FIG. 12) and Epo dose profiles (FIG. 13) for the three representative subject models that were analyzed using SAM. These results thus further confirm the feasibility of SAM as a tool for personalized ESA dosing in anemia management, especially in reducing algorithmic Hemoglobin cycling.

To further validate the usefulness of the SAM, a Monte-Carlo simulation was conducted using a wide range of erythropoietic responses that could be encountered in a clinical setting Briefly, 495 subjects were simulated by a pharmacodynamic model having the following parameters shown in Table 3 below:

TABLE 3

| Erythropoietic response (K) | 0.05 . . . 1.0 g/dL |
|---|---|
| Time Constant (T) | 9, 12, 15 days |
| Random Hb variability | ± 0.5 g/dL |
| Baseline Hb | 7, 8, 9 g/dL |

Each model was simulated twice with Epo doses generated by two different methods (study groups) in order to achieve the target Hb starting from baseline Hb. The simulated Hb response was observed and data collected for a period of 48 weeks (1 year). The study groups included a control group, where Epo dosing is guided by a standard protocol based on the product label and NKF-K/DOQI guidelines; and a treatment group, where Epo dosing guided by the Smart Anemia Manager. The outcomes measured in the study included whether the Hb was within the target concentration of 10-12 g/dL, which was measured as percent Hb values measured between 10 and 12 g/dL after achieving steady-state (16 week), and the Hb variability per subject, which included measuring the standard deviation after achieving steady state (16 weeks).

The study produced the following outcomes shown in Table 4:

TABLE 4

| Hemoglobin Outcomes | Protocol | SAM |
| --- | --- | --- |
| % Hb 10-12 g/dL | 58 | 75 |
| Std Dev Hb per subject | 1.47 (±1.28) | 0.73 (±0.23) |
| Residual Std Dev Hb per subject | 1.93 (±1.11) | 0.76 (±0.18) |

Figure 14:
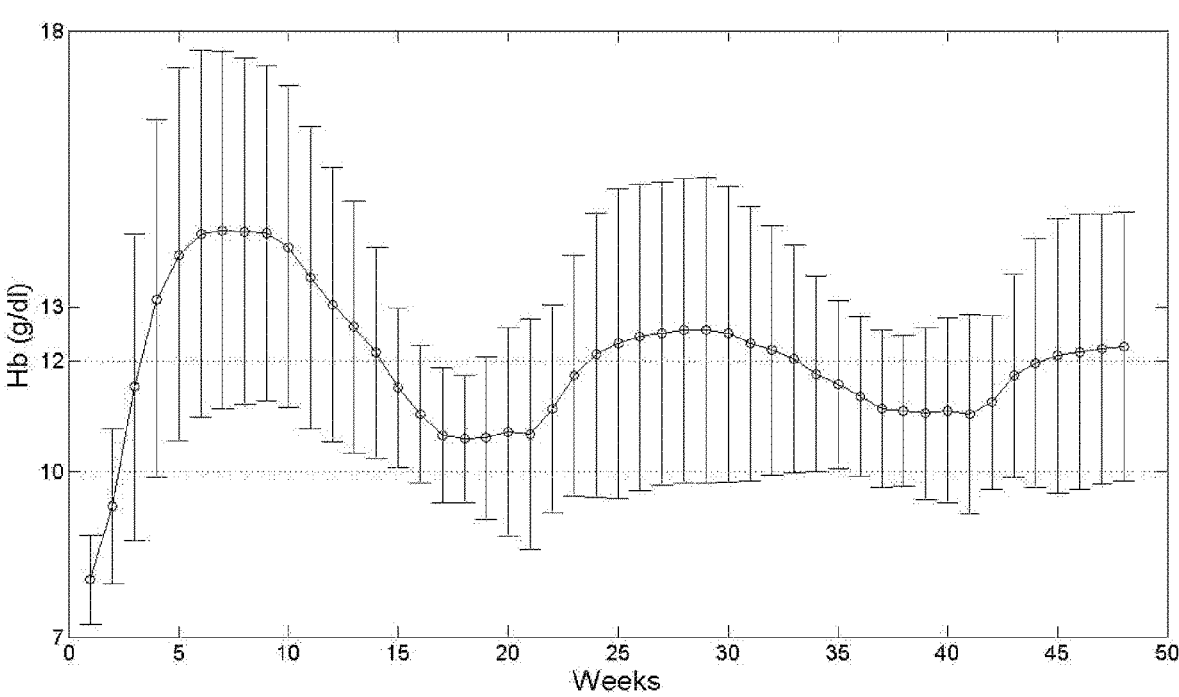
FIG. 14 is a graph of study results for a standard protocol group, and showing a population mean (circles) and standard deviation (error bars) of the simulated Hb responses in the study population when Epo dose was driven by a standard protocol.

FIG. 14 is a graph of the study results for the standard protocol group, and showing a population mean (circles) and standard deviation (error bars) of the simulated Hb responses in the study population when Epo dose was driven by the standard protocol. The large spread of error bars was indicative of large inter-patient variability in the achieved Hb response resulting from suboptimal Epo dosing as performed by the Standard Protocol. The fluctuation of the mean Hb indicated the presence of the undesired phenomenon commonly referred to as "Hb cycling."

Figure 15:
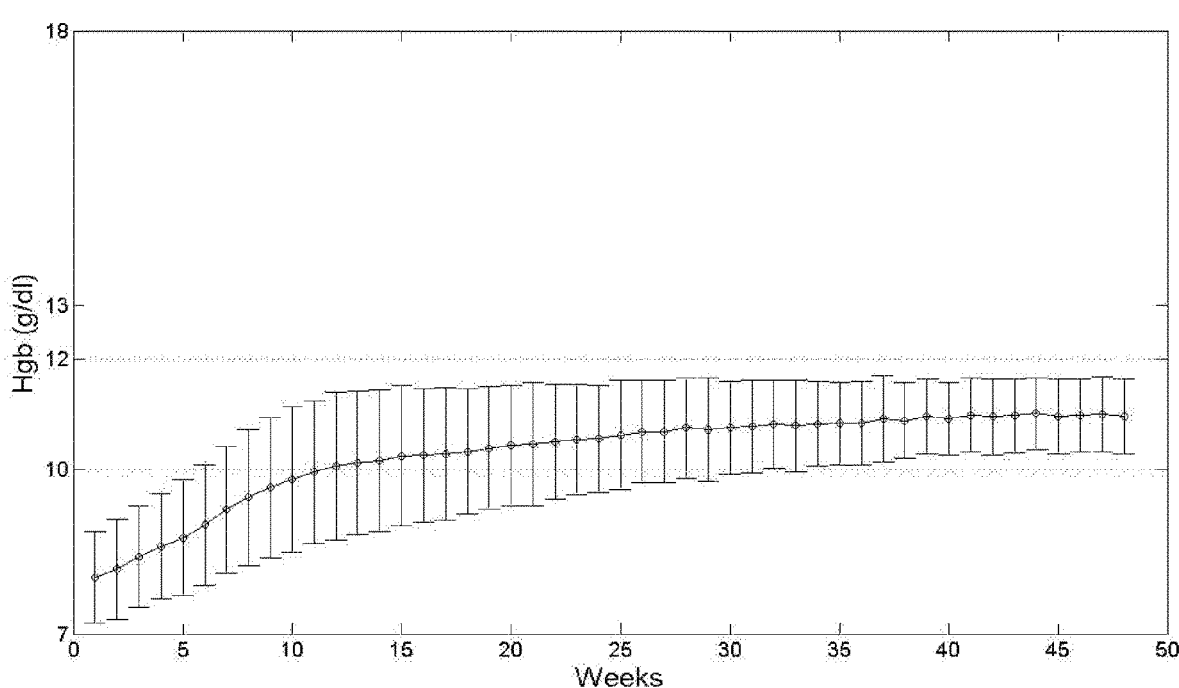
FIG. 15 is a graph of study results for a Smart Anemia Manager group, and showing a population mean and standard deviation of the simulated Hb responses in the study population when Epo dose was driven by the Smart Anemia Manager.

FIG. 15 is a graph of the study results for the Smart Anemia Manager group, and showing a population mean (circles) and standard deviation (error bars) of the simulated Hb responses in the study population when Epo dose was driven by Smart Anemia Manager. Compared to the results achieved by the standard protocol, the error bars in the Smart Anemia Manager Group were much smaller indicating small inter-patient variability in the achieved Hb response. The half-width of the error bars was close to 0.5 g/dL which is the standard deviation of the simulated random variability in Hb. These results thus indicated that the Smart Anemia Manager was robust to random Hb changes, and that, compared to the mean Hb response achieved by the Standard Protocol, the mean Hb response achieved by the Smart Anemia Manager asymptotically approached and remained close to the median of the target range without fluctuations.

Example 4

Double Blind, Randomized Clinical Trial to Assess Personalized Management of Anemia in End Stage Renal Disease Clinically, anemia is a common complication in subjects suffering from End Stage Renal Disease (ESRD), and is frequently associated with decreased quality of life and cardiovascular complications. Anemia is often treated by blood transfusions or, preferably, administration of Erythropoietic Stimulating Agents (ESA). However, effective anemia management in an ESRD population is a complex task because of significant inter-subject variability in erythropoietic response. Furthermore, excessive ESA doses used in hypo-responsive individuals may be associated with increased occurrence of cardiovascular adverse events (see, e.g., Szczech L A, Barnhart H X, Inrig J K, et al. Secondary analysis of the CHOIR trial epoetin-alpha dose and achieved hemoglobin outcomes. Kidney international 2008; 74:791-8). Until recently, the national anemia management guidelines recommended hemoglobin (Hb) target of 10-12 g/dL. Current FDA approved ESA product label no longer recommends Hb target range but stipulates individualized ESA treatment to decrease the risk of blood transfusion. Furthermore, changes in reimbursement rules by Medicare which provides coverage for a large majority of ESRD patients, have led to significant changes in ESA dosing patterns.

As described above, since the introduction of ESAs, dialysis facilities have been providing standardized care using anemia management protocols derived from the national guidelines. The new FDA ruling emphasizes the need for personalized ESA dosing approach (see, e.g., Kliger A S, Fishbane S, Finkelstein F O. Erythropoietic stimulating agents and quality of a patient's life: individualizing anemia treatment. Clin J Am Soc Nephrol 2012; 7:354-7). In this regard, it was believed that a goal of an individualized approach to anemia management should be to maintain a stable Hb at an appropriate level with minimum possible dose-related variability, in order to establish a safety buffer against transfusion.

With regard to individualized approaches to anemia management, it is appreciated that automatic feedback control methods can be applied to ESA dosing (see, e.g., Brier M E, Gaweda A E, Dailey A, Aronoff G R, Jacobs A A. Randomized trial of model predictive control for improved anemia management. Clin J Am Soc Nephrol 2010; 5:814-20; see also Gaweda A E, Jacobs A A, Aronoff G R, Brier M E. Model predictive control of erythropoietin administration in the anemia of ESRD. Am J Kidney Dis 2008; 51:71-9; see also Lines S W, Lindley E J, Tattersall J E, Wright M J. A predictive algorithm for the management of anaemia in haemodialysis patients based on ESA pharmacodynamics: better results for less work. Nephrology, dialysis, transplantation: official publication of the European Dialysis and Transplant Association-European Renal Association 2012; 27:2425-9). As such, the presently-disclosed personalized anemia management approach, guided by the principles of automatic feedback control, was clinically tested to determine whether such an approach improved the maintenance of stable target Hb as compared to standard population-based anemia management protocols.

Briefly, to test whether the maintenance of stable target Hb was improved, a single center, double-blind, standard of care-controlled, parallel group study was performed at the dialysis unit of the Kidney Disease Program, University of Louisville, Louisville, KY. The research protocol conformed to the Declaration of Helsinki and was approved by University of Louisville Institutional Review Board. Informed consent was obtained from each subject before participation in the study. Eligible participants were hemodialysis patients that were: (1) ages 18 to 80; (2) receiving dialysis treatment three times a week; (3) receiving or expected to receive ESA treatment; (4) exhibiting an adequacy of dialysis (Kt/V) of 1.2 or greater; and (5) exhibiting adequate iron stores (Ferritin greater than 200 ng/mL, Transferrin Saturation greater than 20%). Patients were excluded if they: (1) had a life expectancy less than 12 months; (2) were known to suffer from frequent uncontrolled blood loss; (3) were known to suffer from dialyzer clotting; (4) were known to suffer from access related problems; (5) had active infections; (6) were diagnosed with severe cardiac disability; (7) received coronary bypass within three months prior to the beginning of the study; (8) had documented resistance to ESA; or (9) had bone marrow suppression due to HIV, leukemia or pharmacologic agents.

Figure 16:
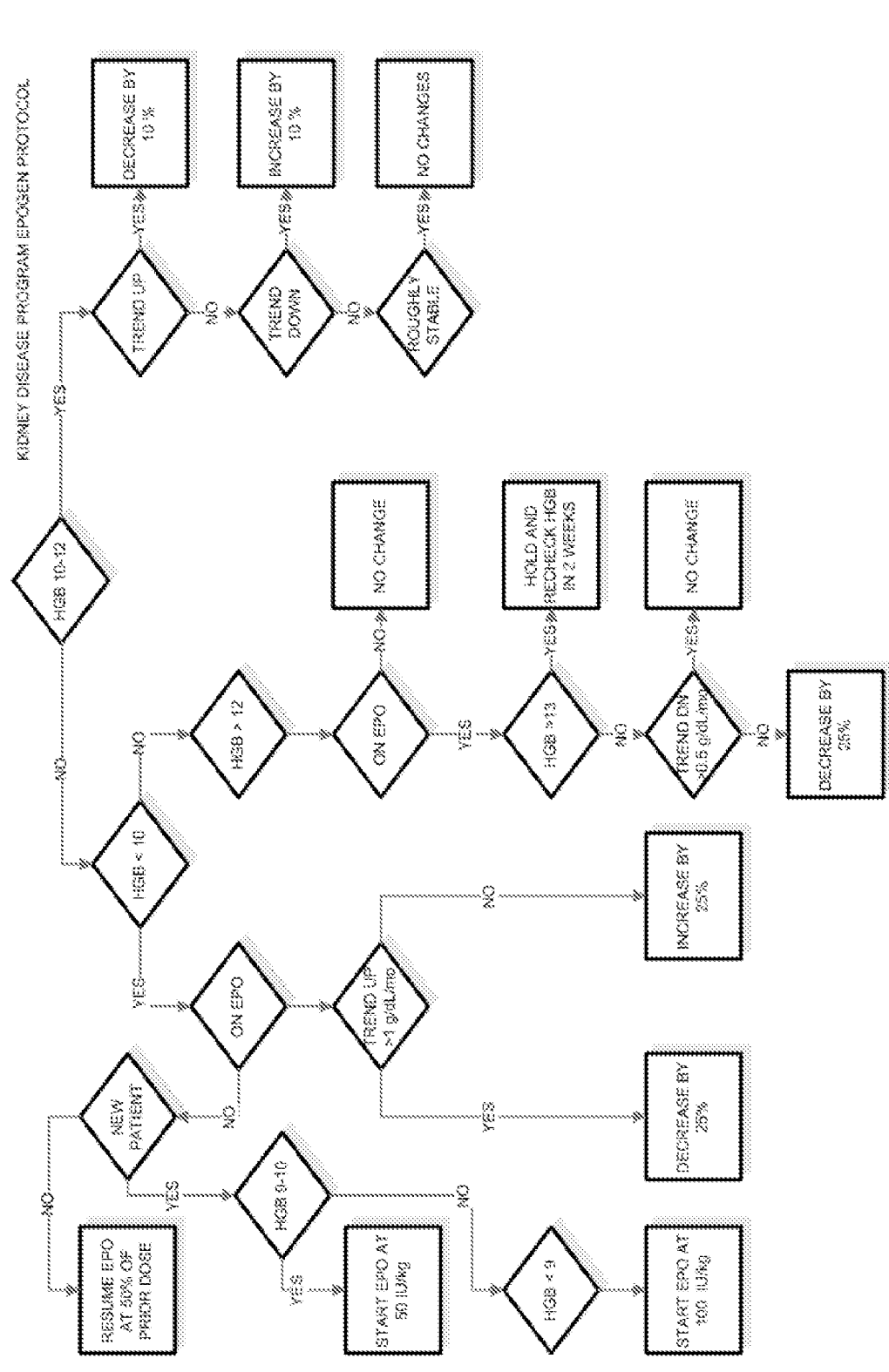
FIG. 16 is a flow chart showing an anemia management protocol used in a control group of a study for assessing a method for the personalized dosing of an erythropoietic stimulating agent according to the present invention.

Subjects were assigned to have their ESA doses guided by "Smart Anemia Manager" (SAM) software or by a standard protocol (FIG. 16). Personalized ESA dosing in SAM was driven by a Multiple Model Predictive Control algorithm, as described above, which designed around individual, dose-response profile dependent ESA adjustment regimens and was designed to drive Hb concentration to, and maintain it, at a patient-specific target value provided by the physician operator, subject to a single dose adjustment not greater than 50% and Hb rate of change of not greater than 2 g/dL per month. Hb concentrations were measured and ESA dose adjustment made at the beginning of each month consistent with the standard of care at the facility. The minimum dose increment was 1,000 IU per week and the maximum allowable dose was 30,000 IU per treatment. The ESA used in the study was epoetin alfa. The Hb target for all subjects in the treatment group was 11 g/dL. The Hb target for all subjects in the control group was between 10 to 12 g/dL. Both targets were consistent with anemia management guidelines at the time of design and implementation of the study.

Monthly ESA dose adjustments were performed by blinded anemia manager nurses. To achieve blinding, the standard protocol used in the control group was programmed into the "Smart Anemia Manager" together with the randomization key. The nurses interacted with the software through a Graphical User Interface which displayed current and historical Hb concentrations over three months, an average weekly ESA dose received over the prior four weeks, and a recommended new weekly ESA dose. The nurses were instructed to follow the dose recommendations unless they found them inappropriate for a particular subject's clinical presentation at the time, in which case they were to consult with the supervising physicians who would then approve or deny overriding the dose recommendation. Intravenous iron sucrose in both groups was administered per a protocol derived from NKF-K/DOQI guidelines. Iron was administered if ferritin was less than 500 ng/mL and TSat was less than 20%. The maximum iron dose was 100 mg 3 times per week. Hospitalization events, diagnosed infections and cardiovascular events, as well as blood transfusions, access complications and procedures were recorded on a weekly basis.

A primary outcome in the study was the proportion (percentage) of Hb concentrations measured within the range 10-12 g/dL over 12 months. That primary outcome was calculated using monthly Hb measurements. If a subject had repeated Hb measurements within a single month due to first Hb of the month outside the target range (per standard practice), only the last measurement was used in the analysis consistent with CMS reporting guidelines.

The study was powered to detect Minimum Clinically Important Difference of 10% in the primary outcome assuming that Hb measurements during the 12-month evaluation period were independent. Assuming efficacy of the standard protocol between 50 and 70%, power analysis was performed using Chi-square test ($\alpha=0.05$, $\beta=0.2$, 2-tailed) and resulted in a conservative sample size estimate of 376 (31.3 subjects) per group.

A total of 62 subjects were enrolled and followed for 12 months between April 2011 and April 2012. Subjects were assigned to treatment or control arm using minimization to balance age, gender, average monthly Hb, median ESA dose, mean TSat, median Ferritin, mean Kt/V, and mean Albumin during the month immediately preceding the study, as well as presence of diabetes, congestive heart failure, and the type of vascular access.

Figure 17:
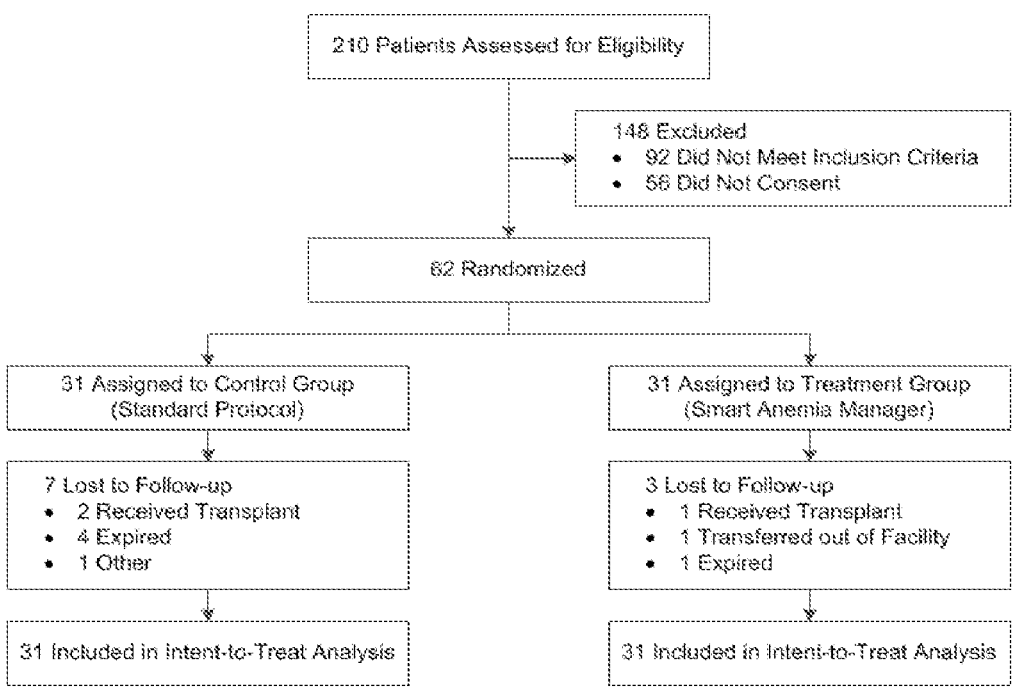
FIG. 17 is a flow chart showing the groups of patients included in a study for assessing a method for the personalized dosing of an erythropoietic stimulating agent according to the presently-disclosed subject matter.

Upon analysis of the results of the study, it was observed that out of the 62 subjects enrolled in the study 52 completed the study, 24 in the control and 28 in the treatment group (FIG. 17), as there were 4 deaths in the control and 1 in the treatment group, three subjects received kidney transplant (2 in the control and 1 in the treatment group), one subject transferred out of the facility, and one subject was dismissed from the study for social issues. The demographic and clinical parameters of the subjects at the beginning of the study are shown in Table 5 below. The groups were similar with the exception of non-significant differences in iron status and ESA dose.

TABLE 5

| Parameter | Control (protocol) | Treatment (SAM) | P |
|---|---|---|---|
| Age (mean ± sdev) | 57 ± 10 | 57 ± 9 | 0.92 |
| Gender | | | 0.79 |
| Male | 22 | 20 | |
| Female | 9 | 11 | |
| Race | | | 0.99 |
| African American | 20 | 21 | |
| Caucasian | 11 | 10 | |
| Hgb (g/dL) (mean ± sdev) | 11.2 ± 1.4 | 11.3 ± 1.0 | 0.68 |
| ESA dose (IU/week) (med ± iqr) | 2000 ± 6000 | 3000 ± 5500 | 0.50 |
| Kt/V (mean ± sdev) | 1.5 ± 0.3 | 1.6 ± 0.2 | 0.75 |
| Albumin (g/dL) (mean ± sdev) | 4.0 ± 0.4 | 4.0 ± 0.3 | 0.91 |
| Transferrin Saturation (%) (mean ± sdev) | 29.5 ± 8.7 | 32.7 ± 11.7 | 0.23 |
| Ferritin (ng/mL) (med ± iqr) | 971 ± 647.5 | 863 ± 528.5 | 0.21 |
| Diabetes | 17 | 18 | 0.99 |
| CHF | 6 | 8 | 0.93 |
| Access: | | | |
| Fistula | 20 | 21 | 0.99 |
| Graft | 6 | 7 | 0.99 |
| Catheter | 5 | 3 | 0.73 |

Figure 18A:
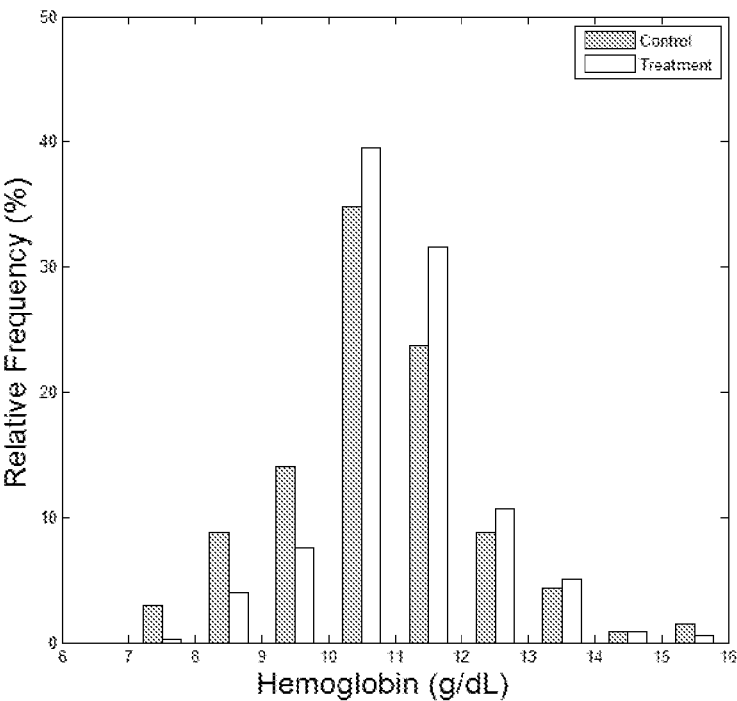
FIGS. 18A-18C are graphs showing the differences in hemoglobin and ESA dosing in subjects whose ESA doses were guided by a standard protocol and in subjects whose ESA doses were guided by a method for the personalized dosing of an erythropoietic stimulating agent according to the presently-disclosed subject matter, including a graph showing the distribution of hemoglobin concentration between study groups (FIG. 18A); a graph showing the ESA dose received between study groups (FIG. 18B); and a graph showing mean individual hemoglobin as a function of mean individual ESA dose (D(mo)—deceased, L(mo)—lost to follow-up, mo—number of months) between study groups.

There were 4 ESA dose recommendation overrides in the control group and no overrides in the treatment group. All overrides were due to perceived insufficient ESA dose at low Hb concentrations. The primary analysis was Intent-To-Treat and included all study subjects. Distribution of monthly Hb concentrations observed in both study groups is shown in FIG. 18A. Subjects in the treatment group had less Hb observations less than 10 g/dL (p<0.001) and more within the 10 to 12 g/dL range (p=0.003), compared to the control group. Both groups had a similar number of Hb observations greater than 12 g/dL (p=0.391). Further, a significant absolute difference of 10.7% in the primary outcome in favor of the treatment group was observed along with a significant absolute difference of 12.9% in the proportion of Hb observations less than 10 g/dL between the groups. Proportions of Hb greater than 12 g/dL were not different between the groups. Mean Hb achieved within the treatment group was 11.0 (±1.2) g/dL, compared to 10.7 (±1.5) g/dL within the control group (p=0.001). Subjects within the treatment group achieved 20% improvement in Hb variability as measured by standard deviation of Hb (p<0.001, per Levene's Test).

Figure 18B:
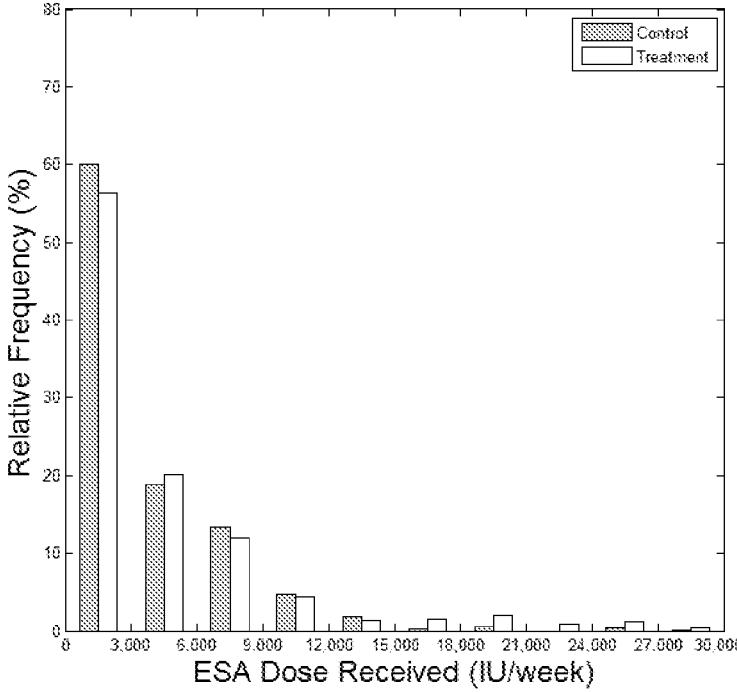

Distribution of weekly ESA dose received in both study groups is shown in FIG. 18B. ESA dose distributions are similar for both groups. (p=0.947, per Mann Whitney U-test, as reported in Table 6 below). Mean ESA dose received by subjects within the treatment group was about 700 IU/week larger (p<0.001) compared to the control group.

TABLE 6

| Parameter | Control | Treatment | P |
|---|---|---|---|
| Proportion Hb 10 to 12 g/dL* | 208/336 (61.9%) | 258/356 (72.5%) | 0.003[a] |
| Proportion Hb less than 10 g/dL | 88/336 (24.7%) | 42/356 (11.8%) | <0.001[a] |
| Proportion Hb greater than 12 g/dL | 46/336 (13.4%) | 56/356 (15.7%) | 0.391[a] |
| Hb (g/dL) (mean ± sdev) | 10.7 ± 1.5 | 11.0 ± 1.2 | 0.001[b] |
| ESA Dose (IU/week) | | | 0.947[c] |
| (mean ± sdev) | 3,033 ± 3,592 | 3,704 ± 5,221 | <0.001[b] |
| (median ± iqr) | 2,000 ± 3,000 | 2,000 ± 5,000 | 0.049[d] |
| Iron Dose (mg/week) | | | 0.462[c] |
| (mean ± sdev) | 28 ± 62 | 24 ± 52 | 0.049[b] |
| (median ± iqr) | 0 ± 0 | 0 ± 0 | 0.714[d] |
| Transferrin Saturation (%) (mean ± sdev) | 30.1 ± 13.13 | 31.6 ± 10.5 | 0.117[b] |
| Ferritin (ng/mL) (median ± iqr) | 905 ± 611 | 868 ± 662 | 0.084[c] |
| Transfusions | | | |
| Subjects | 8 | 5 | 0.065[a] |
| Events | 13 | 6 | 0.115[e] |
| RBC Units | 31 | 21 | 0.169[e] |
| Hospitalizations | | | |
| Subjects | 17 | 17 | 0.999[a] |
| Events | 39 | 41 | 0.824[e] |
| Cardiovascular Adverse Events | | | |
| Subjects | 5 | 9 | 0.226[a] |
| Events | 6 | 9 | 0.455[e] |
| Infections | | | |
| Subjects | 5 | 6 | 0.745[a] |
| Events | 8 | 10 | 0.648[e] |
| Vascular Access Interventions | | | |
| Subjects | 17 | 16 | 0.804[a] |
| Events | 27 | 38 | 0.175[e] |

Figure 18C:
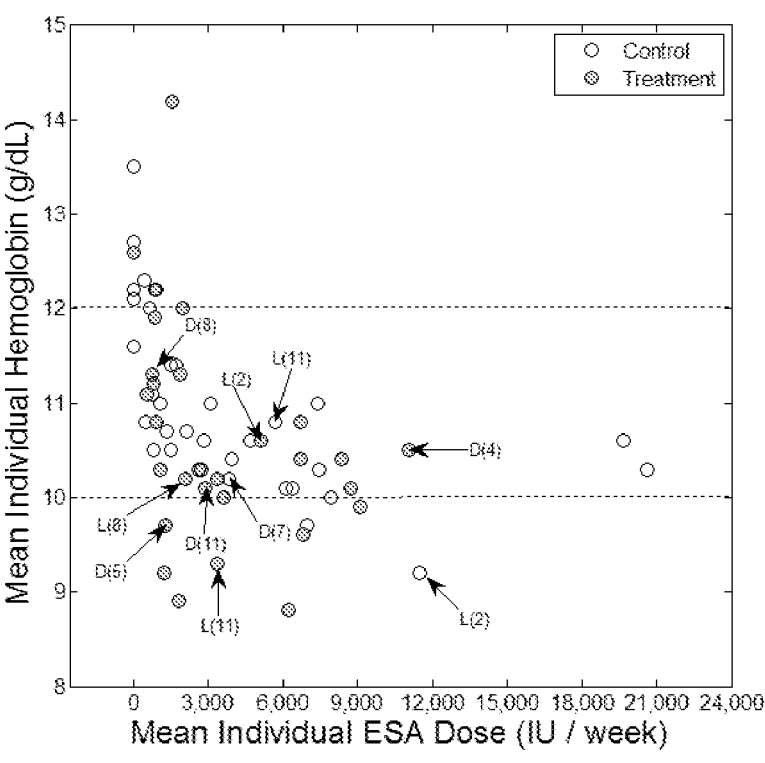

*Primary outcome,
[a] z-test,
[b] t-test,
[c] Mann-Whitney U test,
[d] Independent Samples Median Test,
[e] Binomial Test A scatter plot of mean individual Hb achieved over the course of the study vs. mean individual ESA dose received is shown in FIG. 18C, and provides insight into the outcomes at an individual subject level. 7 out of 31 (22.5%) subjects in the control group achieved mean Hb below 10 g/dL, compared to 2 (6.5%) in the treatment group (p=0.071). 20 subjects (64.5%) in the control group achieved mean Hb between 10 and 12 g/dL, compared to 24 subjects (77.4%) in the treatment group (p=0.266). 4 subjects (12.9%) in the control group and 5 (16.1%) in the treatment group had mean Hb greater than 12 g/dL (p=0.724). 5 subjects did not receive any ESA dose in the course of the study, 1 in the control and 4 in the treatment group. After censoring out these individuals, the proportions of subjects with individual mean Hb below, within, and above target become, 23.3% versus 7.4% (p=0.090), 66.7% vs. 88.9% (p=0.038), and 10% vs. 3.7% (p=0.346), respectively. Among the 3 subjects in the control group with a mean Hb greater than 12 g/dL, only one individual received an incidental ESA dose after suffering hospitalization related blood loss. Throughout the rest of the study, this subject maintained sufficiently high Hb level without the need for ESA. Intra-individual Hb variability as measured by individual standard deviation ranged from 0.1 to 2.2 g/dL in the control group and from 0.2 to 1.4 g/dL in the treatment group.

58 out of 62 subjects (93.5%) received mean ESA dose of less than 10,000 IU per week in the course of the study. Two subjects in the treatment group required mean doses close to 20,000 IU per week. One of these subjects had been diagnosed with congestive heart failure, while the other one suffered peripheral vascular disease and blood losses requiring multiple transfusions for a total of 14 RBC Units.

In terms of iron status, mean iron dose was marginally different (p=0.049) between the study groups and greater by 4 mg/week in the control group. Standard iron markers, TSat and Ferritin, were not different between the groups.

There were 13 transfusion events in 8 subjects for a total of 31 RBC Units in the control group, compared to 6 events, 5 subjects, and 21 RBC Units in the treatment group. Hb thresholds for transfusion ranged between 5.8 and 9.0 g/dL. There were 39 hospitalization events in 17 subjects in the control group and 41 hospitalization events in 17 subjects in the treatment group. There were 6 cardiovascular events in 5 subjects diagnosed within the control group and 9 cardiovascular events in 9 subjects in the treatment group. There were 8 diagnosed infection events in 5 subjects within the treatment group, compared to 10 events in 6 subjects within the treatment group. 17 subjects in the control group underwent 27 vascular access interventions, compared to 16 subjects and 38 interventions in the treatment group.

In the foregoing study, individualization was achieved by using individual ESA dosing regimens designed on the principles of Multiple Model Predictive Control, matched to patients' dose-response profile using data obtained as a part of standard clinical care. From this study, it was observed that individualized administration of ESA leads to an average a 10% improvement in overall Hb stability around a midpoint of the range 10 to 12 g/dL, compared to a standard population-based approach. This improvement was, in part, made possible by: 1) precise achievement of a Hb target, and 2) decreasing Hb variability around the target. Without wishing to be bound by any particular theory, it was believed that these two factors, when combined, led to a significant decrease of Hb concentrations below 10 g/dL without increasing Hb concentrations above 12 d/gL.

Subjects within the treatment group appeared to have received more ESA dose on average as evidenced by statistical measures of central tendency. However, because of a relatively small sample size, those measurements were affected by the inclusion of two erythropoietin resistant individuals within the treatment group, who received ESA doses much larger than the study population as a whole. That finding emphasized the importance of early and aggressive evaluation of the physiologic mechanisms behind ESA resistance and the use of complementary anemia management strategies. Based on the overall results, it was believed that in patients with an otherwise uncompromised erythropoietic response, one can achieve satisfactory anemia correction using weekly ESA dose not greater than 10,000 IU.

Anemia guidelines at the time of study design recommended maintenance of Hb within 10 to 12 g/dL range, and that range was used to design and power the foregoing study. However, significant changes in anemia management have followed recent FDA erythropoietin labeling changes, where the focus has shifted from driving ESA dosing by a standardized Hb target towards more subjective outcomes, such as minimizing the risk of transfusions. In this regard, the approach used above for personalized anemia management was not designed specifically for a Hb target of 10-12 g/dL, although that was the target tested used in this study, but was instead designed primarily to maintain stable Hb at a physician specified target, which can then vary by population or individual.

Finally, no significant or clinically important differences were found between the groups in terms of the recorded significant adverse events. Nevertheless, and although the foregoing study was not powered to detect a difference in the incidence of transfusions, it was found that subjects in the treatment group generally required less transfusions compared to the control group, which was believed to be an indication that the above control process management will be significant in larger populations where transfusions may be required.

Throughout this document, various references are mentioned. All such references are incorporated herein by reference, including the references set forth in the following list:

REFERENCES

1. Brier, et al. "Model Predictive Control of Erythropoietin Administration in the Anemia of ESRD." *Am. J. Kidney Dis.* 2008. 51(1): 71-79.
2. Jacobs, et al. "Randomized Trial of Model Predictive Control for Improved Anemia Management." *Clin. J. Am. Soc. Nephrol.* 2010. 5(5): 814-820.
3. Lacson E, Ofsthun N, Lazarus J M: Effect of variability in anemia management on hemoglobin outcomes in ESRD. *Am. J. Kidney Dis.* 2003. 41: 111-124.
4. National Kidney Foundation: NKF-K/DOQI Clinical Practice, Guidelines for Anemia of Chronic Kidney Disease: Update 2000. *Am. J. Kidney Dis.* 2001. 37: S182-S238, 2001.
5. U.S. Pat. No. 6,056,734, issued May 2, 2000 to Jacobsen, et al., and entitled "Method for Automatic Dosing of Drugs."
6. U.S. Pat. No. 6,267,116, issued Jul. 31, 2001 to McMichael, and entitled "Method and System for Use in Treating a Subject with Any Drug to Optimize Therapy and prevent an Adverse Drug."
7. U.S. Pat. No. 6,575,169, issued Jun. 10, 2003 to McMichael, and entitled "Method and Apparatus for Use in Treating a Subject with Any Drug to Optimize Therapy and Prevent Adverse Drug."
8. U.S. Pat. No. 6,658,396, issued Dec. 2, 2003 to Tang, et al., and entitled "Neural Network Dosage Estimation."
9. U.S. Pat. No. 6,747,002, issued Jun. 8, 2004 to Cheung, et al., and entitled "Pharmacokinetic and Pharmacodynamic Modeling of Erythropoietin Administration."
10. U.S. Pat. No. 6,822,554, issued Nov. 23, 2004 to Vrijens et al., and entitled "Systems and Methods for Medication Monitoring."
11. U.S. Pat. No. 6,883,521, issued Apr. 26, 2005 to McMichael, and entitled "Method and Apparatus for Dosing Single and Multi-Agent Therapy."
12. U.S. Pat. No. 7,232,797, issued Jun. 19, 2007 to Farrell, and entitled "Erythropoietin Dosing Regimen for Treating Anemia."
13. U.S. Pat. No. 7,651,845, issued Jan. 26, 2010 to Doyle, et al., and entitled "Method and Apparatus for Glucose Control and Insulin Dosing for Diabetics."

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method for personalized dosing of a pharmacologic agent to a patient, comprising:
   obtaining a target response value, a current physiologic response value, a current dose value of the pharmacologic agent, past physiologic response values, and past dose values of the pharmacologic agent;
   determining a plurality of dose sets for a respective plurality of dosing regimens based at least in part on the target response value, the current physiologic response value, the current dose value of the pharmacologic agent, the past physiologic response values, and the past dose values of the pharmacologic agent;
   determining a next recommended dose set by combining the plurality of dose sets weighted by degrees of matching; and
   administering the next recommended dose set to the patient;
   wherein the pharmacologic agent is selected from a group comprising erythropoietic stimulating agents, iron supplements, hypoglycemic agents, hypertensive agents, immunosuppressive agents, agents for the treatment of gout, and anticoagulation agents.

2. The method of claim 1, further comprising determining an optimized dose for each of the dosing regimens by:
   determining an optimal dose by iteratively sending a proposed new dose value to a dose-response model function;
   observing a predicted response produced by the dose-response model function; and
   optimizing an objective function value that mathematically formulates treatment objectives.

3. The method of claim 2, further comprising determining the objective function value based on at least one of comparing the predicted response to the target response value, comparing the proposed new dose value to current dose value, comparing the proposed new dose value to a maximum doses value, and comparing a change between the proposed new dose value and the current dose value with a change between the predicted response and the current physiologic response value.

4. The method of claim 1, further comprising determining a number of the plurality of dosing regimens by multiplying a predetermined number of pharmacologic agent sensitivity profiles utilized by a predetermined number of monitoring frequencies utilized.

5. The method of claim 1, further comprising obtaining a response profile; and wherein the degrees of matching are computed using fuzzy sets and the response profile.

6. The method of claim 1, further comprising determining a time of next response measurement as a next time instance at which a current physiologic response value should be measured after the recommended dose set has been implemented.

7. The method of claim 1, wherein the pharmacologic agent is iron supplements and wherein said administering comprises administering intravenously.

8. A system for personalized dosing of a pharmacologic agent comprising:
  an input device;
  a data storage device;
  a plurality of dosing regimen program modules stored on the data storage device, each of the plurality of dosing regimen program modules for determining a dose set;
  a dosing selection algorithm module stored on the data storage device; and
  a processing device in communication with the input device and the data storage device, the processing device:
  executing the plurality of dosing regimen program modules to determine a respective plurality of dose sets in response to receiving from the input device a target response value, a current physiologic response value, a current dose value of the pharmacologic agent, past physiologic response values, and past dose values of the pharmacologic agent for a patient; and
  executing the dosing selection algorithm module, following executing the plurality of dosing regimen program modules and in response to receiving from the input device a response profile of the patient, to determine a next recommended dose set computed as a combination of the plurality of dose sets weighted by degrees of matching computed using at least the response profile;
  wherein the pharmacologic agent is selected from a group comprising erythropoietic stimulating agents, iron supplements, hypoglycemic agents, hypertensive agents, immunosuppressive agents, agents for the treatment of gout, and anticoagulation agents; and
  wherein, after the next recommended dose set is determined, the next recommended dose set is administered to the patient.

9. The system of claim 8, wherein each of the plurality of dosing regimen program modules comprises a dose-response model function and a dose optimizer routine, the dose optimizer routine deriving an optimal dose by iteratively sending a proposed new dose value to the dose-response model function, observing a predicted response produced by the dose-response model function, and optimizing an objective function value that mathematically formulates treatment objectives.

10. The system of claim 9, wherein the objective function value is determined based on at least one of comparing the predicted response to the target response value, comparing the proposed new dose value to current dose value, comparing the proposed new dose value to a maximum doses value, and comparing a change between the proposed new dose value and the current dose value with a change between the predicted response and the current physiologic response value.

11. The system of claim 10, wherein a number of the plurality of dosing regimen program modules is determined by multiplying a predetermined number of pharmacologic agent sensitivity profiles utilized by a predetermined number of monitoring frequencies utilized.

12. The method of claim 8, wherein the degrees of matching are computed using fuzzy sets and the response profile.

13. The system of claim 8, wherein the dosing selection algorithm module further determines a time of next response measurement as a next time instance at which a current physiologic response value should be measured after the recommended dose set has been implemented.

14. A method for personalized dosing of a pharmacologic agent comprising:
  executing, using a processing device, a plurality of dosing regimen program modules to determine a respective plurality of dose sets in response to receiving, from an input device, a target response value, a current physiologic response value, a current dose value of the pharmacologic agent, past physiologic response values, and past dose values of the pharmacologic agent for a patient; and
  executing, using the processing device, a dosing selection algorithm module, following executing the plurality of dosing regimen program modules and in response to receiving from the input device at least a response profile of the patient, to determine a next recommended dose set computed as a combination of the plurality of dose sets weighted by degrees of matching computed using at least the response profile;
  wherein the pharmacologic agent is selected from a group comprising erythropoietic stimulating agents, iron supplements, hypoglycemic agents, hypertensive agents, immunosuppressive agents, agents for the treatment of gout, and anticoagulation agents; and
  wherein, after the next recommended dose set is determined, the next recommended dose set is administered to the patient.

15. The method of claim 14, further comprising a dose optimizer routine of each of the plurality of dosing regimen program modules executing on the processing device, the dose optimizer routine:
  deriving an optimal dose by iteratively sending a proposed new dose value to the dose-response model function;
  observing a predicted response produced by the dose-response model function; and
  optimizing an objective function value that mathematically formulates treatment objectives.

16. The method of claim 15, further comprising determining the objective function value based on at least one of comparing the predicted response to the target response value, comparing the proposed new dose value to current dose value, comparing the proposed new dose value to a maximum doses value, and comparing a change between the proposed new dose value and the current dose value with a change between the predicted response and the current physiologic response value.

17. The method of claim 14, further comprising determining a number of the plurality of dosing regimen program modules by multiplying a predetermined number of pharmacologic agent sensitivity profiles utilized by a predetermined number of monitoring frequencies utilized.

18. The method of claim 14, wherein the degrees of matching are computed using fuzzy sets and the response profile.

19. The method of claim 14, further comprising determining, by the dosing selection algorithm module, a time of next response measurement as a next time instance at which a current physiologic response value should be measured after the recommended dose set has been implemented.

20. A method for personalized dosing of a pharmacologic agent comprising:

executing, using a processing device, a plurality of dosing regimen program modules to determine a respective plurality of dose sets in response to receiving, from an input device, a target response value, a current physiologic response value, a current dose value of the pharmacologic agent, past physiologic response values, and past dose values of the pharmacologic agent for a patient, wherein each of the plurality of dosing regimen program modules has a different dose-response profile; and executing, using the processing device, a dosing selection algorithm module, following executing the plurality of dosing regimen program modules and in response to receiving from the input device a response profile of the patient, to determine a next recommended dose set computed as a combination of the plurality of dose sets weighted by degrees of matching between the dose-response profile of each of the plurality of dosing regimen program modules and the response profile of the patient;

wherein the pharmacologic agent is selected from a group comprising erythropoietic stimulating agents, iron supplements, hypoglycemic agents, hypertensive agents, immunosuppressive agents, agents for the treatment of gout, and anticoagulation agents.

\*  \*  \*  \*  \*